US007767431B2

(12) United States Patent
Liaw et al.

(10) Patent No.: US 7,767,431 B2
(45) Date of Patent: Aug. 3, 2010

(54) *ESCHERICHIA COLI* STRAINS WHICH OVER-PRODUCE L-THREONINE AND PROCESSES FOR THE PRODUCTION OF L-THREONINE BY FERMENTATION

(75) Inventors: Hungming J. Liaw, Champaign, IL (US); Jill S. Bradshaw, Mahomet, IL (US); Yueqin Yang, Decatur, IL (US); Weiying Mao, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 52 days.

(21) Appl. No.: 11/786,818

(22) Filed: Apr. 13, 2007

(65) Prior Publication Data
US 2007/0254337 A1 Nov. 1, 2007

Related U.S. Application Data

(62) Division of application No. 09/962,303, filed on Sep. 26, 2001, now Pat. No. 7,220,571.

(60) Provisional application No. 60/235,884, filed on Sep. 28, 2000.

(51) Int. Cl.
*C12N 9/00* (2006.01)
*C12N 9/02* (2006.01)
*C12N 1/20* (2006.01)
*C12N 15/02* (2006.01)
*C07H 21/02* (2006.01)

(52) U.S. Cl. .................. 435/252.33; 435/183; 435/189; 435/443; 435/444; 435/448; 536/23.1

(58) Field of Classification Search .................. None
See application file for complete search history.

(56) References Cited

U.S. PATENT DOCUMENTS

| 3,375,173 | A | 3/1968 | Nishimura et al. ............ 195/29 |
|---|---|---|---|
| 3,580,810 | A | 5/1971 | Shiio et al. .................... 195/29 |
| 4,321,325 | A | 3/1982 | Debabov et al. ............. 435/115 |
| 4,347,318 | A | 8/1982 | Miwa et al. .................. 435/115 |
| 4,371,615 | A | 2/1983 | Miwa et al. .................. 435/115 |
| 4,463,094 | A | 7/1984 | Chibata et al. ............... 435/115 |
| 4,601,983 | A | 7/1986 | Nakamori et al. ............ 435/115 |
| 4,757,009 | A | 7/1988 | Sano et al. ................... 435/115 |
| 4,764,276 | A | 8/1988 | Berry et al. .................. 210/264 |
| 4,808,317 | A | 2/1989 | Berry et al. .................. 210/660 |
| 4,945,058 | A | 7/1990 | Yanai et al. ............... 435/252.3 |
| 4,946,781 | A | 8/1990 | Nakamori et al. ............ 435/115 |
| 4,980,285 | A | 12/1990 | Sano et al. .................. 435/108 |
| 5,017,483 | A | 5/1991 | Furukawa et al. ............ 435/115 |
| 5,077,207 | A | 12/1991 | Shiio et al. ................... 435/115 |
| 5,087,566 | A | 2/1992 | Takano et al. ................ 435/115 |
| 5,098,835 | A | 3/1992 | Yamada et al. ............... 435/115 |
| 5,153,123 | A | 10/1992 | Terasawa et al. ............. 435/115 |
| 5,164,307 | A | 11/1992 | Yoshihara et al. ............ 435/106 |
| 5,175,107 | A | 12/1992 | Debabov et al. ......... 435/252.33 |
| 5,236,831 | A | 8/1993 | Katsumata et al. ........... 435/106 |
| 5,264,353 | A | 11/1993 | Yamada et al. ............... 435/115 |
| 5,342,766 | A | 8/1994 | Yamada et al. ............... 435/115 |
| 5,474,918 | A | 12/1995 | Kino et al. ................... 435/115 |
| 5,939,307 | A | 8/1999 | Wang et al. ............. 435/252.33 |
| 2003/0113883 | A1 | 6/2003 | Liaw et al. |

FOREIGN PATENT DOCUMENTS

| EP | 0 213 536 A2 | 3/1987 |
|---|---|---|
| EP | 0 593 792 A1 | 4/1994 |
| EP | 0 685 555 A1 | 12/1995 |
| EP | 0 872 547 A1 | 10/1998 |
| JP | 48 077090 A | 10/1973 |
| JP | 53-101591 | 9/1978 |
| WO | WO 98/04715 A1 | 2/1998 |

OTHER PUBLICATIONS

Sen et al. Appl Biochem Biotechnol. Dec. 2007;143(3):212-23.*
Burr, B. et al., "Homoserine Kinase from *Escherichia coli* K12," *Eur. J. Biochem.* 62:519-526, Springer-Verlag (1976).
Cohen, G.N., "The Common Pathway to Lysine, Methionine, and Threonine," in Amino Acids Biosynthesis and Genetic Regulation, Herrmann, K.M. and R.L. Somerville, eds., Addison-Wesley Publishing Company, Reading, Massachusetts, pp. 147-171 (1983).
Falcoz-Kelly, F. et al., "The Methionine-Repressible Homoserine Dehydrogenase and Aspartokinase Activities of *Escherichia coli* K12," *Eur. J. Biochem.* 8:146-152, Springer-Verlag (1969).
Freundlich, M., "Multivalent Repression in the Biosynthesis Of Threonine in *Salmonella typhimurium* And *Escherichia coli*," *Biochem. Biophys. Res. Commun.* 10:277-282, Academic Press (1963).
Gardner, J.F., "Regulation of the threonine operon: Tandem threonine and isoleucine codons in the control region and translational control of transcription termination," *Proc. Natl. Acad. Sci. USA* 76:1706-1710, National Academy of Sciences (1979).
Hashiguchi, K. et al., "Construction of an L-Isoleucine Overproducing Strain of *Escherichia coli* K-12," *Biosci. Biotechnol. Biochem.* 63:672-679, Japan Society for Bioscience, Biotechnology, and Agrochemistry (Apr. 1999).
Hince, T.A. and Neale, S., "Physiological Modification of Alkylating-Agent Induced Mutagenesis. I. Effect Of Growth Rate And Repair Capacity On Nitrosomethylurea-Induced Mutation Of *Escherichia coli*," *Mutat. Res.* 46:1-10, Elsevier/North-Holland Biomedical Press (1977).

(Continued)

*Primary Examiner*—Christian L Fronda
(74) *Attorney, Agent, or Firm*—Craig G. Cochenour; Duane A. Stewart, III; Buchanan Ingersoll & Rooney PC

(57) ABSTRACT

The present invention relates to the fields of microbiology and microbial genetics. More specifically, the invention relates to novel bacteria strains and processes employing these strains for the fermentative production of amino acids such as threonine.

13 Claims, 8 Drawing Sheets

OTHER PUBLICATIONS

Jiao, J. et al., "Molecular analysis of mutations induced by ethylating N-nitroso compounds in the *lacI* gene of *Escherichia coli*," *Mutat. Res.* 352:39-45, Elsevier Science B.V. (1996).

Johnson, E.J. et al., "Threonyl-Transfer Ribonucleic Acid Synthetase and the Regulation of the Threonine operon in *Escherichia coli*," *J. Bacteriol.* 129:66-70, American Society for Microbiology (1977).

Masuda, M. et al., "Improvement of Nitrogen Supply for L-Threonine Production by a Recombinant Strain of *Serratia marcescens*," *Applied Biochem. Biotechnol.* 37:255-262, The Humana Press Inc. (1993).

Nass, G. et al., "Effect Of The Antibiotic Borrelidin On The Regulation Of Threonine Biosynthetic Enzymes in *E. coli*," *Biochem. Biophys. Res. Commun.* 34:84-91, Academic Press (1969).

Nass, G. and Thomale, J., "Alteration Of Structure Or Level Of Threonyl-tRNA-Synthetase In Borrelidin Resistant Mutants of *E. coli*," *FEBS Lett.* 39:182-186, North-Holland (1974).

Okamoto, K. et al., "Hyperproduction of L-Threonine by an *Escherichia coli* Mutant with Impaired L-Threonine Uptake," *Biosci. Biotech. Biochem.* 61:1877-1882, Japan Society for Bioscience, Biotechnology, and Agrochemistry (1997).

Parsot, C. et al., "Nucleotide sequence of *thrC* and of the transcription termination region of the threonine operon in *Escherichia coli* K12," *Nucleic Acids Res.* 11:7331-7345, IRL Press Limited (1983).

Patte, J.-C. et al., "Regulation By Methionine Of The Synthesis Of A Third Aspartokinase And Of A Second Homoserine Dehydrogenase In *Escherichia coli* $K_{12}$," *Biochim. Biophys. Acta* 136:245-257, Elsevier Publishing Company (1967).

Quillardet, P. et al., "Influence of the *uvr*-dependent nucleotide excision repair on DNA adducts formation and mutagenic spectrum of a potent genotoxic agent: 7-methoxy-2-nitronaphtho[2,1- b] furan (R7000)," *Mutat. Res.* 358:113-122, Elsevier (1996).

Sahm, H. et al., "Construction of L-Lysine-, L-Threonine-, or L-Isoleucine- Overproducing Strains of *Corynebacterium glutamicum*," *Annals N.Y. Acad. Sci.* 782:25-39, New York Academy of Sciences (1996).

Shimizu, E. et al., "Culture Conditions for Improvement of L-Threonine Production Using a Genetically Self-cloned L-Threonine Hyperproducing Strain of *Escherichia coli* K-12," *Biosci. Biotech. Biochem.* 59:1095-1098, Japan Society for Bioscience, Biotechnology, and Agrochemistry (1995).

Singer, V.L. et al., "Comparison of SYBR" Green I nucleic acid gel stain mutagenicity and ethidium bromide mutagenicity in the *Salmonella*/mammalian microsome reverse mutation assay (Ames test), *Mutat. Res.* 439:37-47, Elsevier (Feb. 1999).

Thèze, J. and Saint-Girones, I., "Threonine Locus of *Escherichia coli* K-12: Genetic Structure and Evidence for an Operon," *J. Bacteriol.* 118:990-998, American Society for Microbiology (1974).

Thèze, J. et al., "Mapping of the Structural Genes of the Three Aspartokinases and of the Two Homoserine Dehydrogenases of *Escherichia coli* K-12," *J. Bacteriol.* 117:133-143, American Society for Microbiology (1974).

Truffa-Bachi, P. et al., "The Threonine-Sensitive Homoserine Dehydrogenase and Aspartokinase Activities of *Escherichia coli* K 12," *Eur. J. Biochem.* 5:73-80, Springer-Verlag Heidelberg New York on Behalf of the European Biochemical Societies (1968).

Wang, G. and Humayun, M.Z., "Induction of the *Escherichia coli* UVM response by oxidative stress," *Mol. Gen. Genet.* 251:573-579, Springer-Verlag (1996).

Miwa, K. et al., "Construction of L-Threonine Overproducing Strains of *Escherichia coli* K-12 Using Recombinant DNA Techniques," *Agric. Biol. Chem.* 47:2329-2334, The Agricultural Chemical Society of Japan (1983).

Dialog File 351, Accession No. 2060578, Derwent WPI English language abstract for JP 53-101591.

de Boer et al. Proc. Natl Acad Sci USA Jan. 1983; 80(i):21 -5.

Furukawa, S., et al., "Breeding of L-threonine hyper-producer of *Escherichia coli* W," *Appl. Microbiol. Biotechnol.* 29:253-257, Springer-Verlag (1988).

Hirakawa, T., et al., "Mechanism of L-Threonine Production in *E. coli* Auxotrophs," *Agric. Biol. Chem.* 38:77-84, Agricultural Chemical Society of Japan (1974).

Ishida, M., et al., "Improvement of an L-Threonine Producer Derived from *Brevibacterium flavum* Using Threonine Operon of *Escherichia coli* K-12," *Agric. Biol. Chem.* 53:2269-2271, Japan Society for Bioscience, Biotechnology, and Agrochemistry (1989).

Little, S., et al., "Translational Coupling in the Threonine Operon of *Escherichia coli* K-12," *J. Bacteriol.* 171:3518-3522, American Society for Microbiology (1989).

Mizukami, T., et al., "Improvement of the Stability of Recombinant Plasmids Carrying the Threonine Operon in an L-Threonine-hyperproducing Strain of *Escherichia coli* W," *Agric. Biol. Chem.* 50:1019-1028, Agricultural Chemical Society of Japan (1986).

Pátek, M., et al, "Expression of the Threonine Operon from *Escherichia coli* in *Brevibacterium flavum* and *Corynebacterium glutamicum*," *Biotech. Lett.* 11:231-236, Kew, Surrey (1989).

Dialog File 351, WPI Accession No. 1132773, English language abstract for Japanese Patent Application No. JP 48 077090 A (IDS Document AM1), issued Oct. 17, 1979.

International Search Report for International Patent Application No. PCT/US01/30558, mailed Feb. 15, 2002.

\* cited by examiner thr: L-threonine; trf: threonine raffinate

ESCHERICHIA COLI STRAINS WHICH OVER-PRODUCE L-THREONINE AND PROCESSES FOR THE PRODUCTION OF L-THREONINE BY FERMENTATION

CROSS-REFERENCE TO RELATED APPLICATIONS

This application is a divisional application claiming priority to U.S. patent application Ser. No. 09/962,303, which is now U.S. Pat. No. 7,220,571, filed on Sep. 26, 2001, which claimed priority to U.S. Provisional Patent Application No. 60/235,884 filed Sep. 28, 2000. The contents of both of these applications are incorporated by reference as if fully rewritten herein.

BACKGROUND OF THE INVENTION

1. Field of the Invention

The present invention relates to the fields of microbiology and microbial genetics. More specifically, the invention relates to novel bacterial strains and processes employing these strains for fermentative production of amino acids such as L-threonine.

2. Related Art

In *Escherichia coli*, the amino acids L-threonine, L-isoleucine, L-lysine and L-methionine derive all or part of their carbon atoms from aspartate (aspartic acid) via the following common biosynthetic pathway (G. N. Cohen, "The Common Pathway to Lysine, Methionine and Threonine," pp. 147-171 in. *Amino Acids: Biosynthesis and Genetic Regulation*, K. M. Herrmann and R. L. Somerville, eds., Addison-Welesley Publishing Co., Inc., Reading, Mass. (1983)):

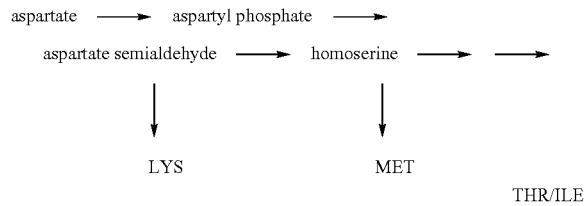

The first reaction of this common pathway is catalyzed by one of three distinct aspartate kinases (AK I, II, or III), each of which is encoded by a separate gene and differs from the others in the way its activity and synthesis are regulated. Aspartate kinase I, for example, is encoded by thrA, its activity is inhibited by threonine, and its synthesis is repressed by threonine and isoleucine in combination. AK II, however, is encoded by metL and its synthesis repressed by methionine (although its activity is not inhibited by methionine or by paired combinations of methionine, lysine, threonine and isoleucine (F. Falcoz-Kelly et al., *Eur. J. Biochem.* 8:146-152 (1969); J. C. Patte et al., *Biochim. Biophys. Acta* 136:245-257 (1967)). AK III is encoded by lysC and its activity and synthesis are inhibited and repressed, respectively, by lysine.

Two of the AKs, I and II, are not distinct proteins, but rather a domain of a complex enzyme that includes homoserine dehydrogenase I or II, respectively, each of which catalyzes the reduction of aspartate semialdehyde to homoserine (P. Truffa-Bachi et al., *Eur. J. Biochem.* 5:73-80 (12968)). Homoserine dehydrogenase I (HD I) is therefore also encoded by thrA, its synthesis is repressed by threonine plus isoleucine and its activity is inhibited by threonine. Homoserine dehydrogenase II (HD II) is similarly encoded by metL and its synthesis is repressed by methionine.

Threonine biosynthesis includes the following additional reactions: Homoserine→Homoserine Phosphate→Threonine. The phosphorylation of homoserine is catalyzed by homoserine kinase, a protein which is composed of two identical 29 kDa subunits encoded for by thrB and whose activity is inhibited by threonine (B. Burr et al., *J. Biochem.* 62:519-526 (1976)). The final step, the complex conversion of homoserine phosphate to L-threonine is catalyzed by threonine synthase, a 47 kDa protein encoded for by thrC (C. Parsot et al., *Nucleic Acids Res.* 11:7331-7345 (1983)).

Isoleucine can be produced in *E. coli* using threonine as a precursor (see Hashiguchi et al., *Biosci. Biotechnol. Biochem.* 63:672-679 (1999). More specifically, isoleucine is produced via the following reactions:

Threonine→α-Ketobutyrate→α-Aceto-α-Hydroxybutyrate→α,β-Dihydroxy-β-Methylvalerate→α-Keto-β-Methylvalerate→Isoleucine. These reactions are catalyzed in *E. coli*, respectively, by the following enzymes: threonine deaminase (ilvA); aceto-hydroxyacid synthetase I, II, or III (ilvBN, ilvGM, and ilvIH, respectively); dihydroxy-acid reductoisomerase (ilvC); dihydroxyacid dehydratase (ilvD); and transaminase-B (ilvE).

The *E. coli* isoleucine operon is composed of ilvA, ilvGM, ilvD, and ilvE. The ilvA gene product (i.e., threonine deaminase) is inhibited by L-isoleucine, and the ilvGM gene product (i.e., aceto-hydroxyacid synthetase II) is inhibited by L-valine. Further, the reactions catalyzed by threonine deaminase and the aceto-hydroxyacid synthetases are believed to be the main rate limiting steps in the production of isoleucine.

The thrA, thrB and thrC genes all belong to the thr operon, a single operon located at 0 minutes on the genetic map of *E. coli* (J. Thèze and I. Saint-Girons, *J. Bacteriol.* 118:990-998 (1974); J. Thèze et al., *J. Bacteriol.* 117:133-143 (1974)). These genes encode, respectively, for aspartate kinase I-homoserine dehydrogenase I, homoserine kinase and threonine synthase. Biosynthesis of these enzymes is subject to multivalent repression by threonine and isoleucine (M. Freundlich, *Biochem. Biophys. Res. Commun.* 10:277-282 (1963)).

A regulatory region is found upstream of the first structural gene in the thr operon and its sequence has been determined (J. F. Gardner, *Proc. Natl. Acad. Sci. USA* 76:1706-1710 (1979)). The thr attenuator, downstream of the transcription initiation site, contains a sequence encoding a leader peptide; this sequence includes eight threonine codons and four isoleucine codons. The thr attenuator also contains the classical mutually exclusive secondary structures which permit or prevent RNA polymerase transcription of the structural genes in the thr operon, depending on the levels of the charged threonyl- and isoleucyl-tRNAs.

Because of the problems associated with obtaining high levels of amino acid production via natural biosynthesis (e.g., repression of the thr operon by the desired product), bacterial strains have been produced having plasmids containing a thr operon with a thrA gene that encodes a feedback-resistant enzyme. With such plasmids, L-threonine has been produced on an industrial scale by fermentation processes employing a wide variety of microorganisms, such as *Brevibacterium flavum*, *Serratia marcescens*, and *E. coli*.

For example, the *E. coli* strain BKIIM B-3996 (Debabov et al., U.S. Pat. No. 5,175,107), which contains the plasmid pVIC40, makes about 85 g/L in 36 hr. The host is a threonine-requiring strain because of a defective threonine synthase. In BKIIM B-3996, it is the recombinant plasmid, pVIC40, that provides the crucial enzymatic activities, i.e., a feedback-resistant AK I-HD I, homoserine kinase and threonine synthase, needed for threonine biosynthesis. This plasmid also complements the host's threonine auxotrophy.

E. coli strain 29-4 (E. Shimizu et al., Biosci. Biotech. Biochem. 59:1095-1098 (1995)) is another example of a recombinant E. coli threonine producer. Strain 29-4 was constructed by cloning the thr operon of a threonine-over-producing mutant strain, E. coli K-12 (βIM-4) (derived from E. coli strain ATCC Deposit No. 21277), into plasmid pBR322, which was then introduced into the parent strain (K. Wiwa et al., Agric. Biol. Chem. 47:2329-2334 (1983)). Strain 29-4 produces about 65 g/L of L-threonine in 72 hr.

Similarly constructed recombinant strains have been made using other organisms. For example, the Serratia marcescens strain T2000 contains a plasmid having a thr operon which encodes a feedback-resistant thrA gene product and produces about 100 g/L of threonine in 96 hrs (M. Masuda et al., Applied Biochem. Biotechn. 37:255-262 (1992)). All of these strains contain plasmids having multiple copies of the genes encoding the threonine biosynthetic enzymes, which allows over-expression of these enzymes. This over-expression of the plasmid-borne genes encoding threonine biosynthetic enzymes, particularly a thrA gene encoding a feedback-resistant AK I-HD I, enables these strains to produce large amounts of threonine. Other examples of plasmid-containing microorganisms are described, for example, in U.S. Pat. Nos. 4,321,325; 4,347,318; 4,371,615; 4,601,983; 4,757,009; 4,945,058; 4,946,781; 4,980,285; 5,153,123; and 5,236,831.

Plasmid-containing strains such as those described above, however, have problems that limit their usefulness for commercial fermentative production of amino acids. For example, a significant problem with these strains is ensuring that the integrity of the plasmid-containing strain is maintained throughout the fermentation process because of potential loss of the plasmid during cell growth and division. To avoid this problem, it is necessary to selectively eliminate plasmid-free cells during culturing, such as by employing antibiotic resistance genes on the plasmid. This solution, however, necessitates the addition of one or more antibiotics to the fermentation medium, which is not commercially practical for large scale fermentations Another significant problem with plasmid-containing strains is plasmid stability. High expression of enzymes whose genes are coded on the plasmid, which is necessary for commercially practical fermentative processes, often brings about plasmid instability (E. Shimizu et al., Biosci. Biotech. Biochem. 59:1095-1098 (1995)). Plasmid stability is also dependent upon factors such as cultivation temperature and the level of dissolved oxygen in the culture medium. For example, plasmid-containing strain 29-4 was more stable at lower cultivation temperatures (30° C. vs. 37° C.) and higher levels of dissolved oxygen (E. Shimizu et al., Biosci. Biotech. Biochem. 59:1095-1098 (1995)).

Non-plasmid containing microorganisms, while less efficacious than those described above, have also been used as threonine producers. Strains of E. coli such as H-8460, which is obtained by a series of conventional mutagenesis and selection for resistance to several metabolic analogs makes about 75 g/L of L-threonine in 70 hours (Kino et al., U.S. Pat. No. 5,474,918). Strain H-8460 does not carry a recombinant plasmid and has one copy of the threonine biosynthetic genes on the chromosome. The lower productivity of this strain compared to the plasmid-bearing strains, such as BKIIM B-3996, is believed to be due to lower enzymatic activities (particularly those encoded by the thr operon) as these non-plasmid containing strains carry only a single copy of threonine biosynthetic genes.

An L-threonine producing strain of E. coli, KY10935, produced by multiple rounds of mutation is described in K. Okamoto et al., Biosci. Biotechnol. Biochem. 61:1877-1882 (1997). When cultured under optimal conditions with DL-methionine, strain KY10935 is reported to produce as much as 100 g/liter L-threonine after 77 hours of cultivation. The high level of L-threonine produced is believed to result from the inability of this strain to take up L-threonine that accumulates extracellularly, resulting in a decrease in the steady-state level of intracellular L-threonine and the release the remaining regulatory steps in the L-threonine production pathway from feedback inhibition.

Other examples of suitable non-plasmid containing microorganisms are described, for example, in U.S. Pat. Nos. 5,939,307; 5,474,918; 5,264,353; 5,164,307; 5,098,835; 5,087,566; 5,077,207; 5,017,483; 4,463,094; 3,580,810; and 3,375,173.

In both the non-plasmid and plasmid containing strains of E. coli, the thr operon is controlled by the particular strain's respective native threonine promoter. As described above, the expression of the native promoter is regulated by an attenuation mechanism controlled by a region of DNA which encodes a leader peptide and contains a number of threonine and isoleucine codons. This region is translated by a ribosome which senses the levels of threoninyl-tRNA and isoleucinyl-tRNA. When these levels are sufficient for the leader peptide to be translated, transcription is prematurely terminated, but when the levels are insufficient for the leader peptide to be translated, transcription is not terminated and the entire operon is transcribed, which, following translation, results in increased production of the threonine biosynthetic enzymes. Thus, when threonyl-tRNA and/or isoleucinyl-tRNA levels are low, the thr operon is maximally transcribed and the threonine biosynthetic enzymes are maximally made.

In the E. coli threonine-producing strain BKIIM B-3996, the threonine operon in the plasmid is controlled by its native promoter. As a result, the thr operon is only maximally expressed when the strain is starved for threonine and/or isoleucine. Since starvation for threonine is not possible in a threonine-producing strain, these strains have been rendered auxotrophic for isoleucine in order to obtain a higher level of enzymatic activity.

Another way of overcoming attenuation control is to lower the level(s) of threonyl-tRNA and/or isoleucinyl-tRNA in the cell. A thrS mutant, for example, having a threonyl-tRNA synthase which exhibits a 200-fold decreased apparent affinity for threonine, results in over-expression of the thr operon, presumably due to the low level of threonyl-tRNA (E. J. Johnson et al., J. Bacteriol. 129:66-70 (1977)).

In fermentation processes using these strains, however, the cells must be supplemented with isoleucine in the growth stage because of their deficient isoleucine biosynthesis. Subsequently, in the production stage, the cells are deprived of isoleucine to induce expression of the threonine biosynthetic enzymes. A major drawback, therefore, of using native threonine promoters to control expression of the threonine biosynthetic enzymes is that the cells must be supplemented with isoleucine.

The antibiotic borrelidin, a natural product of Streptomyces rochei, is also known to reduce the enzymatic activity of threonyl tRNA-synthetase, and thereby inhibit the growth of E. coli (G. Nass et al., Biochem. Biophys. Res. Commun. 34:84 (1969)). In view of this reduced activity, certain borrelidin-sensitive strains of E. coli have been employed to produce high levels of threonine (Japanese Published Patent Application No. 6752/76; U.S. Pat. No. 5,264,353). Addition of borrelidin to the culture was found to increase the yield of L-threonine. Borrelidin-sensitive strains of *Brevibacterium* and *Corynebacterium* have also been used to produce high levels of threonine (Japanese Patent No. 53-101591).

Borrelidin-resistant mutants of *E. coli* similarly exhibit changes in threonyl tRNA-synthetase activity. More specifically, borrelidin-resistant *E. coli* have been shown to exhibit one of the following features: (i) constitutively increased levels of wild-type threonyl tRNA-synthetase; (ii) structurally altered threonyl tRNA-synthetase; or (iii) some unknown cellular alteration, probably due to a membrane change (G. Nass and J. Thomale, *FEBS Lett.* 39:182-186 (1974)). None of these mutant strains, however, has been used for the fermentative production of L-threonine.

*E. coli* strains have recently been described which contain chromosomally integrated thr operons under the regulatory control of a non-native promoter (Wang et al., U.S. Pat. No. 5,939,307, the entire disclosure of which is incorporated herein by reference). One of these strains, ADM Kat13, was shown to produce as much as 102 g/L of L-threonine after 48 hours in culture.

There remains a need in the art for microorganism strains which are readily culturable and efficiently produce large amounts of amino acids such as threonine and isoleucine.

SUMMARY OF THE INVENTION

One object of the present invention is to provide microorganisms which efficiently produce amino acids (e.g., L-threonine) in large amounts and high yields. In general, microorganisms of the invention do not require any recombinant plasmids containing genes that encode enzymes in the biosynthesis of the amino acid product and, in most instances, have no amino acid nutritional requirements.

When bacterial strains of the invention over-produce L-threonine, in many instances, these strains will be resistant to either L-threonine itself or threonine raffinate (TRF).

In one embodiment, the invention is directed to processes for producing *Escherichia coli* strains capable of producing between about 95 and about 150 g/L of L-threonine by about 48 hours of growth in culture comprising:

(a) inserting into the chromosome of an *E. coli* at least one threonine operon operably linked to a non-native promoter to produce a parent strain; and (b) performing at least one cycle of mutagenesis on the parent strain, followed by screening the mutagenized cells to identify *E. coli* which produce between about 95 and about 150 g/L of L-threonine by about 48 hours of growth in culture. The invention also includes *E. coli* strains produced by the above processes.

In related embodiments, the invention is directed to processes for producing *E. coli* strains capable of producing between about 110 and about 120 g/L of L-threonine, between about 110 and about 130 g/L of L-threonine, or between about 100 and about 140 g/L of L-threonine by about 48 hours of growth in culture.

In additional related embodiments, the invention is directed to processes for producing *E. coli* strains employing agents such as alkylating agents, intercalating agents, and ultraviolet light to induce mutations.

In other related embodiments, the invention is directed to processes for producing *E. coli* strains having two or three threonine operons inserted into the chromosome of the *E. coli*. Further, these individual threonine operons may be operably linked to at least two different non-native promoters. Non-native promoters suitable for use in the invention include the tac promoter, the lac promoter, the trp promoter, the lpp promoter, the $P_L$ promoter, and the $P_R$ promoter.

Related embodiments also include processes for producing *E. coli* strains having threonine operons containing genes that encode feedback-resistant aspartate kinase-homoserine dehydrogenases. Further, *E. coli* strains used to generate strains of the invention may contain a defective threonine dehydrogenase gene on their chromosomes.

Strains which may be used in the processes discussed above include those which contain a threonine operon obtained from the *E. coli* strain deposited as ATCC Deposit No. 21277.

The processes described above may also be used to generate strains which are resistant to threonine raffinate, resistant to borrelidin or cyclopentanecarboxylic acid (CPCA), or resistant to any combination of threonine raffinate, borrelidin and CPCA. Thus, the invention also includes strains of *E. coli* produced by the above process which are resistant to threonine raffinate, resistant to borrelidin or CPCA, or resistant to any combination of threonine raffinate, borrelidin and CPCA.

In other embodiments the invention is directed to *E. coli* strains comprising at least one chromosomally integrated threonine operon operably linked to a non-native promoter. These strains are capable of producing between about 110 and about 120 g/L of L-threonine, between about 110 and about 130 g/L of L-threonine, between about 100 and about 140 g/L of L-threonine, or between about 95 and about 150 g/L of L-threonine by about 48 hours of growth in culture. Strains of the invention will generally not include *E. coli* strains KY10935, ADM TH1.2, and ADM Kat13.

In related embodiments, the invention includes *E. coli* strains which have the above characteristics and comprise a threonine operon obtained from the *E. coli* strain deposited as ATCC Deposit No. 21277.

The invention also includes *E. coli* strains which are resistant to threonine raffinate and are capable of producing between about 110 and about 120 g/L of L-threonine, between about 110 and about 130 g/L of L-threonine, between about 100 and about 140 g/L of L-threonine, or between about 95 and about 150 g/L of L-threonine by about 48 hours of growth in culture.

In other embodiments, the threonine operon of *E. coli* strains of the invention encodes a feedback-resistant aspartate kinase I-homoserine dehydrogenase I gene (thrA), a homoserine kinase (thrB) gene, and a threonine synthase gene (thrC).

In further embodiments, *E. coli* strains of the invention contain a defective threonine dehydrogenase gene on their chromosomes.

The invention also includes *E. coli* strains which have the characteristics of the strain deposited as NRRL B-30319 (Agriculture Research Culture Collection (NRRL), 1815 N. University Street, Peoria, Ill., 61604, USA).

The invention further includes the *E. coli* strains deposited as NRRL B-30316, NRRL B-30317, NRRL B-30318, and NRRL B-30319 (Agriculture Research Culture Collection (NRRL), 1815 N. University Street, Peoria, Ill., 61604, USA).

Additionally, the invention is directed to processes for producing L-threonine comprising the steps of culturing the strains mentioned above and recovering L-threonine produced.

DETAILED DESCRIPTION OF THE PREFERRED EMBODIMENTS

Figure 1:
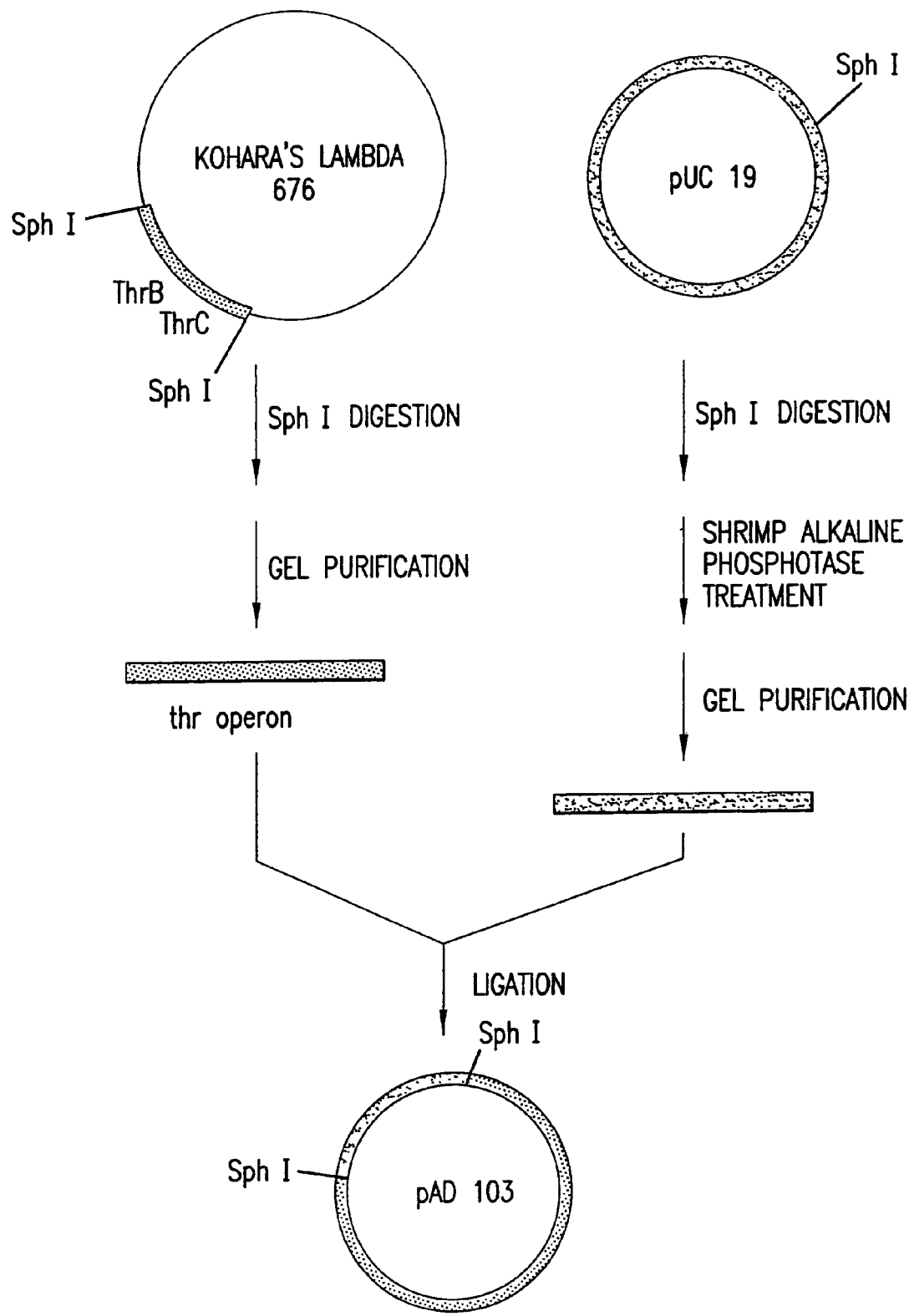
FIG. 1 depicts the construction of plasmid pAD103 from Kohara's lambda 676 and plasmid pUC19.
Figure 2:
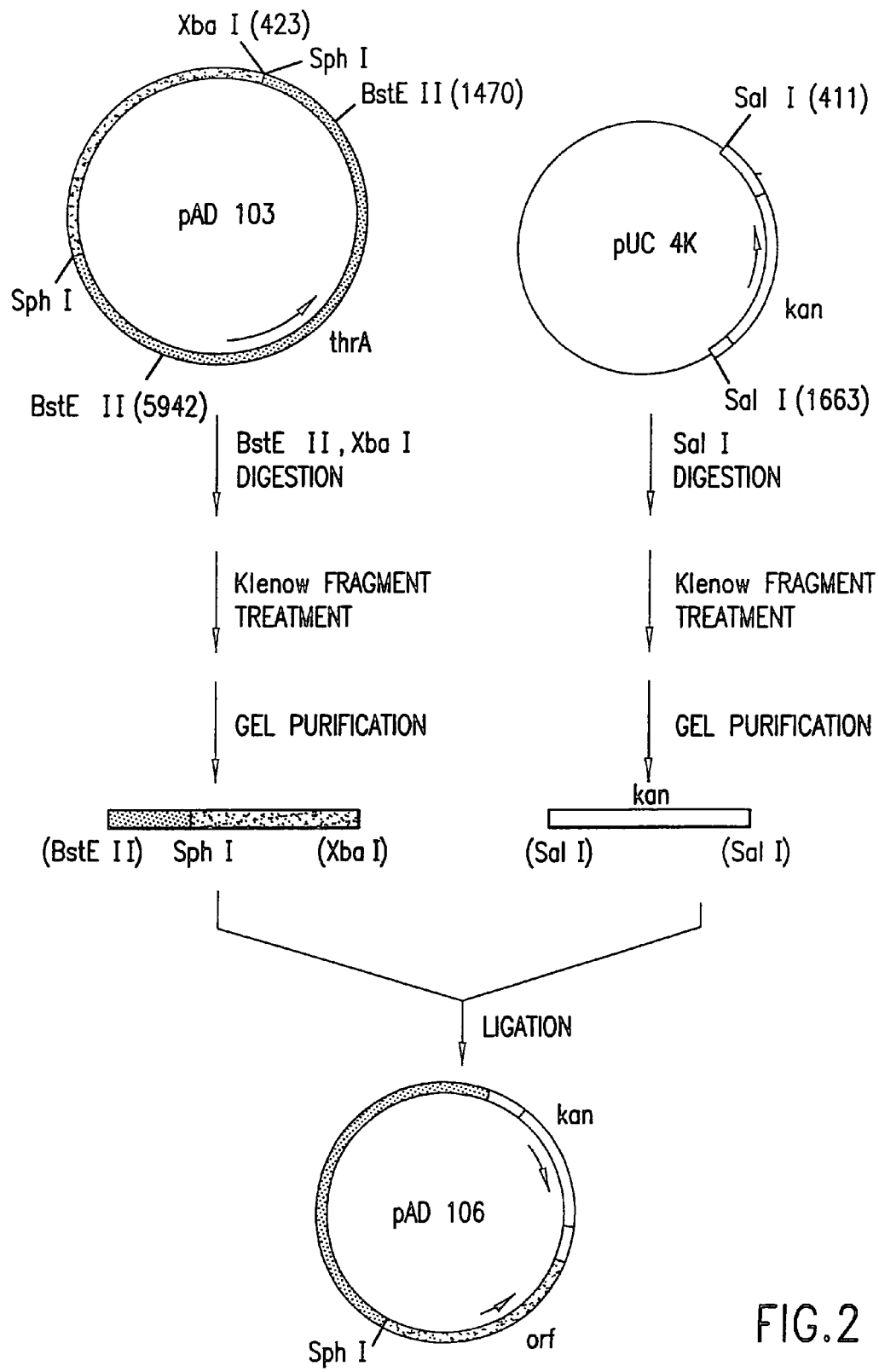
FIG. 2 depicts the construction of plasmid pAD106 from plasmid pAD103 and plasmid pUC4k.
Figure 3:
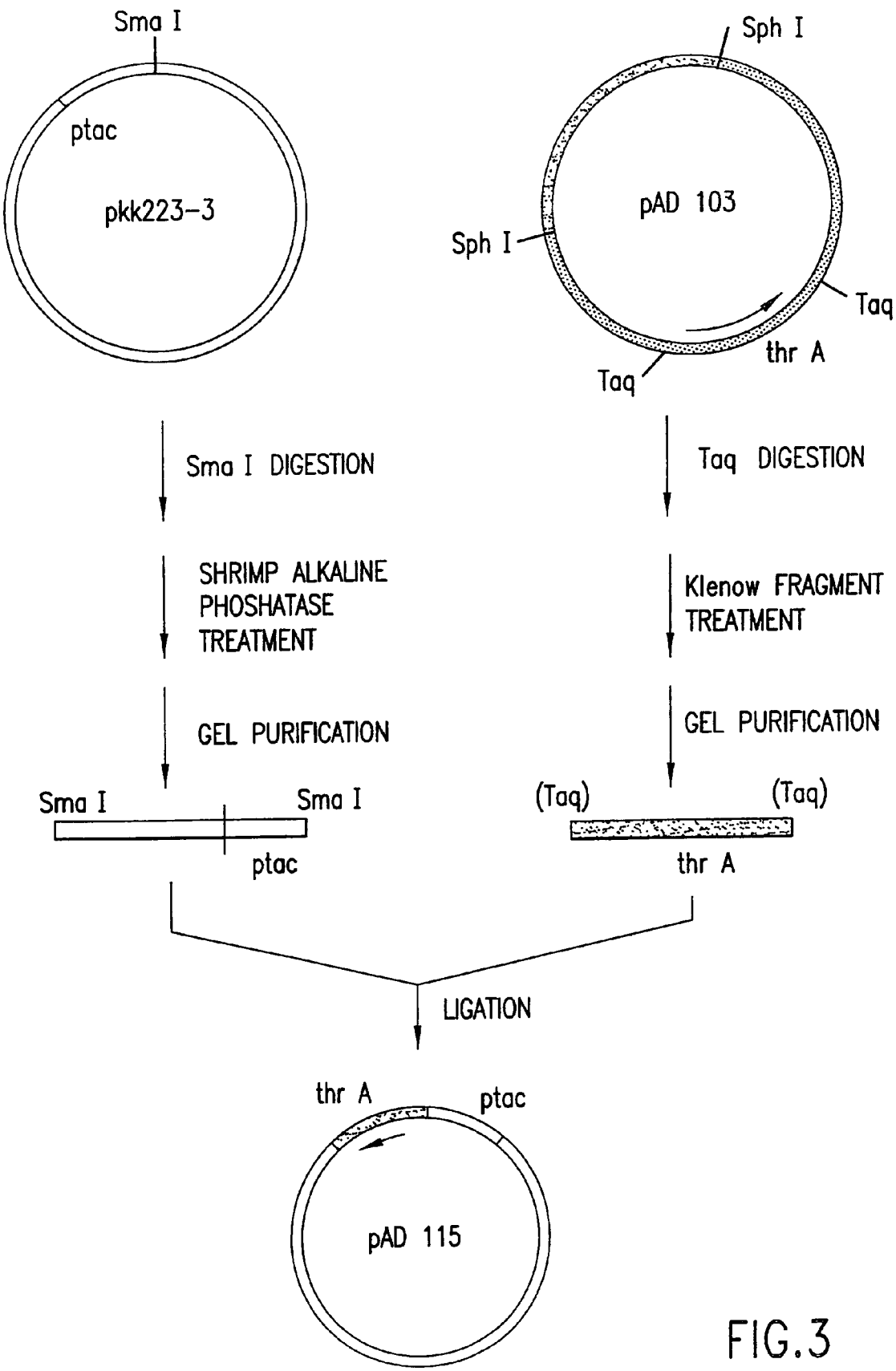
FIG. 3 depicts the construction of plasmid pAD115 from plasmid pAD103 and plasmid pkk223-3.
Figure 4:
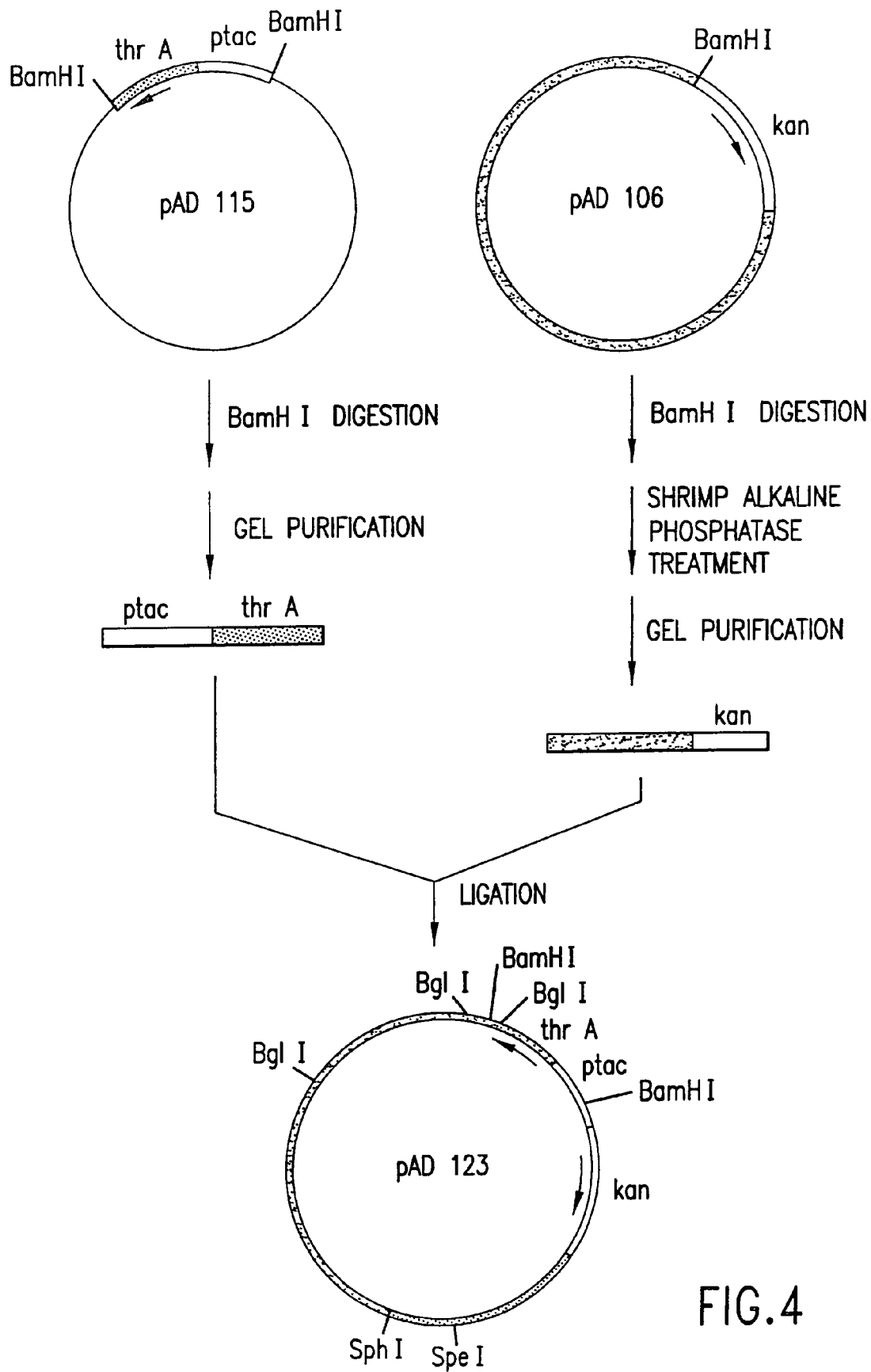
FIG. 4 depicts the construction of plasmid pAD123 from plasmid pAD115 and plasmid pAD106.
Figure 5:
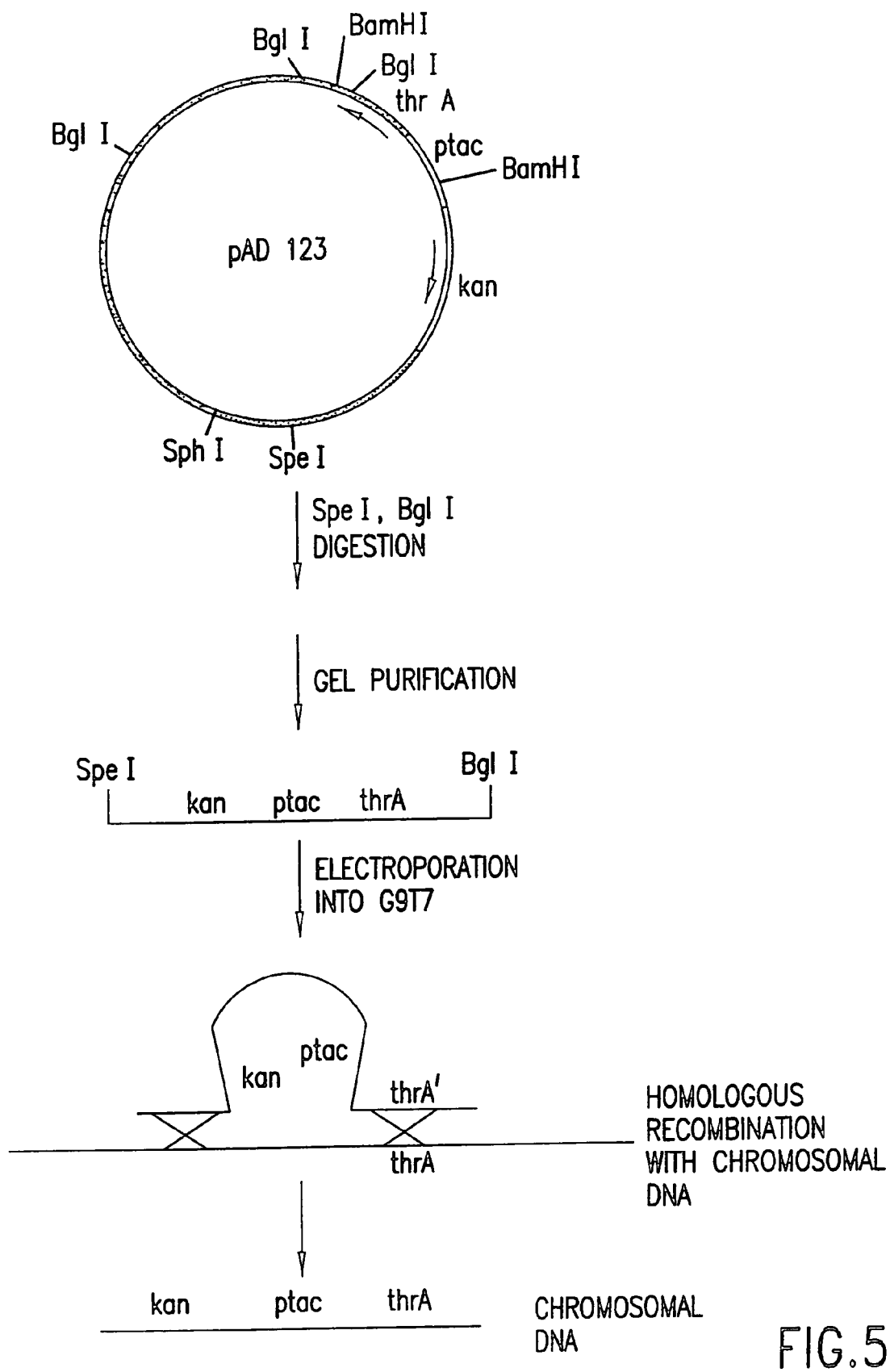
FIG. 5 depicts the integration of the promoter region from plasmid pAD123 into the chromosome of E. coli.

The present invention provides strains of novel microorganisms which, when grown in culture, produce relatively large amounts of amino acids (e.g., L-threonine and L-isoleucine). Further provided are methods for producing the aforementioned strains and methods for producing amino acids (e.g., L-threonine and L-isoleucine) using these strains. Thus, the invention is directed, in part, to novel bacterial strains which may be used in fermentation processes for the production of amino acid such as L-threonine or L-isoleucine.

In one aspect, the invention provides bacterial strains (e.g., strains of E. coli) which demonstrate both resistance to raffinate and improved growth properties. These bacterial strains allow for the production of amino acids in high amounts and yields.

A number of alterations can be made to bacterial cells which alter their metabolism and confer upon them the ability to produce increased quantities of amino acids and other metabolic products. Examples of such alterations include the following:

1. Eliminating or reducing feedback control mechanisms of one or more biosynthetic pathways which lead to the production of amino acids or amino acid precursors.

2. The enhancement of metabolic flow by either amplifying or increasing the expression of genes which encode rate-limiting enzymes of biosynthetic pathways that lead to the production of amino acids or amino acid precursors.

3. Inhibiting degradation of a desired amino acid end product or one or more intermediates and/or precursors of the desired amino acid end product.

4. Increasing the production of amino acid intermediates and/or and precursors.

5. When the pathway which leads to production of a desired amino acid end product is branched, inhibiting branches which do not lead to the amino acid to increase intermediate and/or precursor availability.

6. Altering membrane permeability to optimize uptake of energy molecules (e.g., glucose), intermediates and/or precursors.

7. Altering membrane permeability to optimize amino acid end product excretion.

8. The enhancement of growth tolerance to relatively high concentrations of end products (e.g., amino acids), metabolic waste products (e.g., acetic acid), or metabolic side products (e.g., amino acid derivatives either formed by the bacterial themselves or formed in the culture medium) which are inhibitory to bacterial cell growth.

9. The enhancement of resistance to high osmotic pressure during culturing resulting from high concentrations of carbon sources (e.g., glucose) or end products (e.g., amino acids).

10. The enhancement of growth tolerance to changes in environmental conditions (e.g., pressure, temperature, pH, etc.).

11. Increasing activities of enzymes involved in the uptake and use of carbon sources in the culture medium (e.g., raffinose, stachyose or proteins, as well as other components of corn steep liquor).

Bacteria optimized for production of a particular end product (e.g., L-threonine) will generally differ from wild-type bacteria by having multiple characteristics (e.g., two of more characteristics set out in the list above) which lead to increased production of the desired end product. The invention thus includes methods for producing bacterial strains which exhibit properties set out above and produce increased amounts of amino acids as compared to wild-type strains. The invention also includes bacterial strains produced by the methods disclosed herein.

I. DEFINITIONS

The following definitions are provided to clarify the subject matter which the inventors consider to be the present invention.

As used herein, the term "yield" refers to the amount of a product produced in relation to the amount of a starting material. With respect to amino acids produced by a microorganism, yield refers to the amount of amino acid produced with respect to the amount of intermediate, precursor or nutrient provided. For example, when 100 grams of dextrose is supplied to a microorganism which produces 25 grams of L-isoleucine, the yield of L-isoleucine, with respect to the dextrose, is 25%.

As used herein, the term "raffinate" refers to wastestream products generated from ion-exchange operations for amino acid recovery from fermentation broth in which bacteria have been cultured.

As used herein, the phrase "threonine raffinate (TRF)" refers to wastestream products generated from ion-exchange operations for threonine recovery from fermentation broth in which bacteria that produce threonine have been cultured.

As one skilled in the art would recognize, TRF is a heterogenous composition, the content of which will vary with a number of factors (e.g., the composition of the initial culture medium, the nutritional requirements of the cultivated organism(s), metabolic products produced by the cultivated organism(s), and chromatographic preparation process used). For purposes of selecting and identifying bacteria which are resistant to TRF, TRF will generally have the characteristics set out herein in Section II.

As used herein, the term "strain" refers to bacteria of a particular species which have common characteristics. Unless indicated to the contrary, the terms "strain" and "cell" are used interchangeably herein. As one skilled in the art would recognize, bacterial strains are composed of individual bacterial cells. Further, individual bacterial cells have specific characteristics (e.g., a particular level of resistance to TRF) which identifies them as being members of their particular strain.

As used herein, the term "mutation" refers to an insertion, deletion or substitution in a nucleic acid molecule. When present in the coding region of a nucleic acid, a mutation may be "silent" (i.e., results in no phenotypic effect) or may alter the function of the expression product of the coding region. When a mutation occurs to the regulatory region of a gene or operon, the mutation may either have no effect or alter the expression characteristics of the regulated nucleic acid.

As used herein, the term "mutagenesis" refers to a process whereby one or more mutations are generated in an organism's genetic material (e.g., DNA). With "random" mutagenesis, the exact site of mutation is not predictable, occurring anywhere in the chromosome of the microorganism. Further, with random mutagenesis, the mutations are generally brought about as a result of physical damage to the organism's nucleic acid caused by agents such as radiation or chemical treatment. As discussed in more detail below, numerous agents may be used to perform mutagenesis.

As used herein, the phrase "cycle of mutagenesis" in general refers to the treatment of cells with a mutagen, or combination of mutagens, followed by culture of those cells to allow surviving cells to reproduce. In many instances, the mutagenized cells will be screened to identify those with particular characteristics after each cycle of mutagenesis. Further, as part of a cycle of mutagenesis, cells treated with a mutagen may be exposed to a selective agent (e.g., TRF) immediately after mutagenesis or while still exposed to the mutagen.

As used herein, the term "phenotype" refers to observable physical characteristics dependent upon the genetic constitution of a microorganism. Examples of phenotypes include the ability to express particular gene products and the ability to produce certain amounts of a particular amino acid in a specified amount of time.

As used herein, the term "over-produce" refers to the production of a compound by a cell in an amount greater than the amount produced by a reference strain (e.g., a parent strain). One example of an over-producing strain would be a strain generated from a parent strain (i.e., the reference strain) using mutagenesis which produces more L-threonine than the parent. Thus, the strain generated by mutagenesis would "over-produce" L-threonine in comparison to the parent, reference strain.

As used herein, the term "operon" refers to a unit of bacterial gene expression and regulation. Operons are generally composed of regulatory elements and at least one open reading frame (ORF). An example of an operon is the threonine operon of *E. coli* which is composed of a regulatory region and three open reading frames. Another example of an operon is the isoleucine operon of *E. coli* which is composed of a regulatory region and four open reading frames.

As used herein, the term "parent strain" refers to a strain of a microorganism subjected to mutagenesis to generate a microorganism of the invention. Thus, use of the phrase "parent strain" does not necessarily equate with the phrase "wild-type" or provide information about the history of the referred to strain.

II. STRAINS OF THE INVENTION AND THEIR PREPARATION

Novel bacterial strains of the present invention have the following characteristics:

(1) they contain at least one operon which (a) is integrated into the bacterial chromosome, (b) is under the control of a non-native promoter, and (c) encodes enzymes involved in amino acid synthesis; and (2) they are capable of producing one or more amino acids upon growth in culture.

In particular embodiments, novel bacterial strains of the present invention include strains which have the following characteristics:

(1) they contain at least one thr operon (i.e., contain at least one set of the genes encoding threonine biosynthetic enzymes) which (a) is integrated into the bacterial chromosome and (b) is under the control of a non-native promoter; and (2) they are capable of producing either L-threonine or L-isoleucine upon growth in culture.

A. Operons Suitable for Use with the Invention

While, as explained below, the invention can be used to produce cells which over-produce a considerable number of amino acids, the invention is discussed below mainly with respect to cells which over-produce L-threonine and L-isoleucine, as well as processes for producing these amino acids.

The threonine (thr) operon on the chromosome of cells of bacterial strains included within the scope of the invention encodes enzymes necessary for threonine biosynthesis. Due to the fact that several enzymes are capable of catalyzing reactions to produce various intermediates in the threonine pathway, the genes present in the threonine operon employed can vary. For example, the threonine operon can be composed of an AK-HD gene (thrA or metL), a homoserine kinase gene (thrB), and a threonine synthase gene (thrC). Further, the thr operon can be composed of thrA (the AK I-HD I gene), thrB and thrC. Suitable thr operons may be obtained, for example, from *E. coli* strains deposited with the American Type Culture Collection (ATCC), 10801 University Blvd., Manassas, Va. 20110-2209, USA and assigned ATCC Deposit Nos. 21277 and 21530.

Further, multiple copies of the thr operon may be present on the chromosomes of bacterial cells of the invention. Increased copy number of the thr operon will generally result in increased expression of the genes of this operon upon induction.

In many instances, the thr operon contains at least one non-attenuated gene (i.e., expression of the gene is not suppressed by the levels (extra- and/or intra-cellular) of one or more of the threonine biosynthetic enzymes and/or the products thereof (e.g., L-threonine and L-isoleucine)). The inventive strains may also contain a thr operon having a defective thr attenuator (the regulatory region downstream of the transcription initiation site and upstream of the first structural gene) or a thr operon that lacks the thr attenuator altogether.

In one specific embodiment, the thr operon encodes one or more feedback-resistant threonine biosynthetic enzymes (e.g., the activity of the enzyme is not inhibited by the extra- and/or intra-cellular levels of the intermediates and/or products of threonine biosynthesis). In a more specific embodiment, the thr operon contains a gene that encodes a feedback-resistant AK-HD, such as a feedback-resistant AK I-ID I. Use of a feedback-resistant AK-HD provides a higher level of enzymatic activity for threonine biosynthesis, even in the presence of the L-threonine being produced.

Expression of the threonine operon(s) in strains of the invention will generally be controlled by a non-native promoter (i.e., a promoter that does not control expression of the thr operon in bacterial strains normally found in nature). Replacing the native promoter of the threonine biosynthetic enzymes with a strong non-native promoter to control expression of the thr operon results in higher threonine production even with only a single, genomic copy of the thr operon. In addition, when a non-native promoter is used to control expression of threonine operon, it is not necessary to render the bacterial strains auxotrophic for isoleucine to achieve this higher threonine production. Illustrative examples of promoters suitable for use in *E. coli* include, but are not limited to: the lac promoter, the trp promoter, the $P_L$ promoter of λ bacteriophage, the $P_R$ promoter, the lpp promoter, and the tac promoter. In one specific embodiment, the tac promoter is used.

In addition to the threonine operon, cells of the inventive bacterial strains may also contains at least one gene encoding aspartate semialdehyde dehydrogenase (asd) either integrated into their chromosomes or present on an extrachromosomal element (e.g., a plasmid). For example, the chromosome in cells of the present invention may contain at least one asd gene, at least one thrA gene, at least one thrB gene and/or at least one thrC gene. Of course, one, two, three, or more copies of each of these genes may be present.

Threonine dehydrogenase (tdh) catalyzes the oxidation of L-threonine to α-amino-β-ketobutyrate. Accordingly, in one specific embodiment, the chromosome of the inventive cells further contains at least one defective threonine dehydrogenase (tdh⁻) gene. The defective tdh gene may be a gene having a reduced level of expression of threonine dehydrogenase or a gene that encodes a threonine dehydrogenase mutant having reduced enzymatic activity relative to that of native threonine dehydrogenase. For example, the defective tdh gene employed in inventive strains does not express threonine dehydrogenase. Illustrative examples of suitable tdh⁻ genes that do not express threonine dehydrogenase include a tdh gene having a chloramphenicol acetyltransferase (cat) gene inserted into it or a tdh gene having transposon Tn5 inserted into it, as described in U.S. Pat. No. 5,175,107.

The invention further provides microorganisms which express increased amounts of enzymes which catalyze the production of L-isoleucine, as well as microorganisms which over-produce L-isoleucine. As one skilled in the art, bacterial strains of the invention which produce increased quantities of L-threonine, in effect, allow for the production of substantial quantities of L-isoleucine. This is so because, as already discussed, L-threonine is a precursor of L-isoleucine. Thus, operons suitable for use with the present invention include the isoleucine operon of *E. coli*, which is composed of the ilvA, ilvGM, ilvD, and ilvE genes.

In one embodiment of the invention, an isoleucine operon under the control of a non-native promoter is introduced into microorganisms. Further, nucleic acid encoding dihydroxy-acid reductoisomerase (ilvC) may also be introduced into cells. These genes may be either inserted into chromosomal DNA or carried on plasmids.

In addition, because the reactions catalyzed by threonine deaminase and aceto-hydroxyacid synthetase are believed to be the rate limiting steps in the production of isoleucine, it will be advantages, when the production of isoleucine is desired, to over-express these particular gene products.

In addition, because the gene products of the ilvA gene (i.e., threonine deaminase) and the ilvGM (i.e., aceto-hydroxyacid synthetase II) are inhibited, respectively, by L-isoleucine and L-valine, in many circumstances, it will generally be advantageous to use feed-back resistant forms of these enzymes.

Similar modifications of cells and process of the invention can be readily employed to produce other amino acids generated by pathways related to those for the production of L-threonine and L-isoleucine. Examples of amino acids which can be produced using such modifications include L-lysine and L-glycine.

The invention also provides microorganisms which express increased amounts of enzymes which catalyze the production of L-methionine, as well as microorganisms which over-produce L-methionine. Examples of such microorganisms are ones which contain at least one met operon on the chromosome (i.e., the metL gene (which encodes AK II-HD II), the metA gene (homoserine succinyltransferase), the metB gene (cystathionine γ-synthase), the metC gene (cystathionine β-lyase) and the metE and metH genes (homocysteine methylase)) that have been subjected to mutagenesis and screening steps described herein. The genes set out in the preceding sentence, including feedback-resistant variants thereof, and, optionally, a non-native promoter can be introduced into the chromosome of the host microorganism according to one or more of the general methods discussed herein and/or known to those skilled in the art.

As indicated above, microorganisms which over-produce lysine can also be prepared by subjecting microorganisms that contain genes encoding lysine biosynthetic enzymes (e.g., a feedback-resistant lysine biosynthetic enzyme encoded by lysC and/or dapA) and, optionally, a non-native promoter to mutagenesis and screening steps described herein.

Bacterial strains of the present invention may be prepared by any of the methods and techniques known and available to those skilled in the art. Illustrative examples of suitable methods for constructing the inventive bacterial strains include gene integration techniques (e.g., mediated by transforming linear DNA fragments and homologous recombination) and transduction mediated by the bacteriophage P1. These methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989), the entire disclosure of each of which is incorporated herein by reference.

B. Amino Acid Production

Bacterial strains of the present invention include strains which are capable of producing substantial quantities of L-threonine or L-isoleucine when grown in culture. In particular, when grown in culture, strains of the invention include strains which are capable of producing at least about 65 g/L of L-threonine in about 36 hours, at least about 75 g/L of L-threonine in about 36 hours, at least about 85 g/L of L-threonine in about 36 hours, at least about 95 g/L of L-threonine in about 36 hours, at least about 105 g/L of L-threonine in about 36 hours, at least about 110 g/L of L-threonine in about 36 hours, at least about 115 g/L of L-threonine in about 36 hours, at least about 120 g/L of L-threonine in about 36 hours, at least about 125 g/L of L-threonine in about 36 hours, at least about 130 g/L of L-threonine in about 36 hours, at least about 135 g/L of L-threonine in about 36 hours, at least about 140 g/L of L-threonine in about 36 hours, at least about 145 g/L of L-threonine in about 36 hours, or at least about 150 g/L of L-threonine in about 36 hours. Further, the inventive strains include strains which are capable of producing at least about 95 g/L of L-threonine in about 48 hours, at least about 100 g/L of L-threonine in about 48 hours, at least about 105 g/L of L-threonine in about 48 hours, at least about 110 g/L of L-threonine in about 48 hours, at least about 115 g/L of L-threonine in about 48 hours, at least about 120 g/L of threonine in about 48 hours, at least about 125 g/L of L-threonine in about 48 hours, at least about 130 g/L of L-threonine in about 48 hours, at least about 135 g/L of L-threonine in about 48 hours, at least about 140 g/L of L-threonine in about 48 hours, at least about 145 g/L of L-threonine in about 48 hours, or at least about 150 g/L of threonine in about 48 hours.

Further, the inventive strains include strains which are capable of producing L-threonine at a rate of at least about 2 g/L/hr, at least about 2.5 g/L/hr, at least about 3 g/L/hr, at least about 3.6 g/L/hr, at least about 4.0 g/L/hr, at least about 4.5 g/L/hr, or at least about 5.0 g/L/hr.

In addition, when grown in culture, the inventive strains include strains which are capable of producing between about 75 and about 95 g/L of L-threonine in about 36 hours, between about 80 and about 100 g/L of L-threonine in about 36 hours, between about 85 and about 105 g/L of L-threonine in about 36 hours, between about 90 and about 110 g/L of L-threonine in about 36 hours, between about 95 and about 110 g/L of L-threonine in about 36 hours, between about 100 and about 15 g/L of L-threonine in about 36 hours, between about 100 and about 120 g/L of L-threonine in about 36 hours, between about 100 and about 125 g/L of L-threonine in about 36 hours, between about 100 and about 130 g/L of L-threonine in about 36 hours, between about 100 and about 135 g/L of L-threonine in about 36 hours, between about 100 and about 140 g/L of L-threonine in about 36 hours, between about 105 and about 120 g/L of L-threonine in about 36 hours, between about 110 and about 120 g/L of L-threonine in about 36 hours, between about 110 and about 125 g/L of L-threonine in about 36 hours, between about 110 and about 130 g/L of L-threonine in about 36 hours, between about 110 and about 135 g/L of L-threonine in about 36 hours, between about 110 and about 140 g/L of L-threonine in about 36 hours, between about 115 and about 130 g/L of L-threonine in about 36 hours, between about 120 and about 135 g/L of L-threonine in about 36 hours, between about 95 and about 115 g/L of L-threonine in about 36 hours, between about 95 and about 120 g/L of L-threonine in about 36 hours, between about 95 and about 125 g/L of L-threonine in about 36 hours, between about 95 and about 135 g/L of L-threonine in about 36 hours, between about 95 and about 145 g/L of L-threonine in about 36 hours, between about 95 and about 150 g/L of L-threonine in about 36 hours, between about 105 and about 125 g/L of L-threonine in about 36 hours, between about 105 and about 130 g/L of L-threonine in about 36 hours, or between about 105 and about 135 g/L of L-threonine in about 36 hours.

Further, when grown in culture, the inventive strains include strains which are capable of producing between about 80 and about 100 g/L of L-threonine in about 48 hours, between about 85 and about 105 g/L of L-threonine in about 48 hours, between about 90 and about 110 g/L of L-threonine in about 48 hours, between about 95 and about 110 g/L of L-threonine in about 48 hours, between about 100 and about 115 g/L of L-threonine in about 48 hours, between about 105 and about 120 g/L of L-threonine in about 48 hours, between about 110 and about 125 g/L of L-threonine in about 48 hours, between about 115 and about 130 g/L of L-threonine in about 48 hours, between about 120 and about 135 g/L of L-threonine in about 48 hours, between about 125 and about 140 g/L of L-threonine in about 48 hours, between about 95 and about 115 g/L of L-threonine in about 48 hours, between about 95 and about 120 g/L of L-threonine in about 48 hours, between about 95 and about 125 g/L of L-threonine in about 48 hours, between about 95 and about 135 g/L of L-threonine in about 48 hours, between about 95 and about 145 g/L of L-threonine in about 48 hours, between about 95 and about 150 g/L of L-threonine in about 48 hours, between about 100 and about 120 g/L of L-threonine in about 48 hours, between about 100 and about 125 g/L of L-threonine in about 48 hours, between about 100 and about 130 g/L of L-threonine in about 48 hours, between about 100 and about 135 g/L of L-threonine in about 48 hours, between about 100 and about 140 g/L of L-threonine in about 48 hours, between about 100 and about 145 g/L of L-threonine in about 48 hours, between about 105 and about 125 g/L of L-threonine in about 48 hours, between about 105 and about 130 g/L of L-threonine in about 48 hours, between about 105 and about 135 g/L of L-threonine in about 48 hours, between about 105 and about 140 g/L of L-threonine in about 48 hours, between about 105 and about 145 g/L of L-threonine in about 48 hours, between about 105 and about 150 g/L of L-threonine in about 48 hours, between about 110 and about 120 g/L of L-threonine in about 48 hours, between about 110 and about 130 g/L of L-threonine in about 48 hours, between about 110 and about 135 g/L of L-threonine in about 48 hours, between about 110 and about 140 g/L of L-threonine in about 48 hours, between about 115 and about 125 g/L of L-threonine in about 48 hours, between about 115 and about 135 g/L of L-threonine in about 48 hours, between about 115 and about 140 g/L of L-threonine in about 48 hours, between about 115 and about 145 g/L of L-threonine in about 48 hours, or between about 115 and about 150 g/L of L-threonine in about 48 hours.

The bacterial strains of the invention also include strains which produce L-threonine in high yield with respect to the carbon source present in the culture medium. Thus, the strains of the invention include strains which, with reference to the dextrose content of the culture medium, produce L-threonine in the following yields (wt./wt.): about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

Strains of the invention include strains which, with reference to the dextrose content of the culture medium, produce L-threonine in the following ranges of yields (wt./wt.): between about 25% and about 40%, between about 30% and about 35%, between about 30% and about 45%, between about 30% and about 50%, between about 35% and about 40%, between about 35% and about 45%, between about 35% and about 50%, between about 40% and about 45%, and between about 40% and about 50%.

Strains of the invention include strains which are capable of producing at least about 65 g/L of L-isoleucine in about 36 hours, at least about 75 g/L of L-isoleucine in about 36 hours, at least about 85 g/L of L-isoleucine in about 36 hours, at least about 95 g/L of L-isoleucine in about 36 hours, at least about 105 g/L of L-isoleucine in about 36 hours, at least about 115 g/L of L-isoleucine in about 36 hours, at least about 125 g/L of L-isoleucine in about 36 hours, at least about 130 g/L of L-isoleucine in about 36 hours, at least about 135 g/L of L-isoleucine in about 36 hours, or at least about 140 g/L of L-isoleucine in about 36 hours. Further, the inventive strains include strains which are capable of producing at least about 90 g/L of L-isoleucine in about 48 hours, at least about 100 g/L of L-isoleucine in about 48 hours, at least about 110 g/L of L-isoleucine in about 48 hours, at least about 120 g/L of L-isoleucine in about 48 hours, at least about 130 g/L of L-isoleucine in about 48 hours, at least about 140 g/L of L-isoleucine in about 48 hours, or at least about 150 g/L of L-isoleucine in about 48 hours.

Further, the inventive strains include strains which are capable of producing L-isoleucine at a rate of at least about 2 g/L/hr, at least about 2.5 g/L/hr, at least about 3 g/L/hr, at least about 3.6 g/L/hr, at least about 4.0 g/L/hr, at least about 4.5 g/L/hr, or at least about 5.0 g/L/hr.

In addition, when grown in culture, the inventive strains include strains which are capable of producing between about 75 and about 95 g/L of L-isoleucine in about 36 hours, between about 85 and about 105 g/L of L-isoleucine in about 36 hours, between about 95 and about 115 g/L of L-isoleucine in about 36 hours, between about 105 and about 125 g/L of L-isoleucine in about 36 hours, between about 115 and about 135 g/L of L-isoleucine in about 36 hours, or between about 125 and about 145 g/L of L-isoleucine in about 36 hours.

Further, when grown in culture, the inventive strains include strains which are capable of producing between about 80 and about 100 g/L of L-isoleucine in about 48 hours, between about 85 and about 105 g/L of L-isoleucine in about 48 hours, between about 90 and about 110 g/L of L-isoleucine in about 48 hours, between about 100 and about 120 g/L of L-isoleucine in about 48 hours, between about 110 and about 130 g/L of L-isoleucine in about 48 hours, between about 120 and about 140 g/L of L-isoleucine in about 48 hours, or between about 130 and about 150 g/L of L-isoleucine in about 48 hours.

The bacterial strains of the invention also include strains which produce L-isoleucine in high yield with respect to the carbon source present in the culture medium. Thus, the strains of the invention include strains which, with reference to the dextrose content of the culture medium, produce L-isoleucine in the following yields (wt./wt.): about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

Strains of the invention include strains which, with reference to the dextrose content of the culture medium, produce L-isoleucine in the following ranges of yields (wt./wt.): between about 25% and about 40%, between about 30% and about 35%, between about 30% and about 45%, between about 30% and about 50%, between about 35% and about 40%, between about 35% and about 45%, between about 35% and about 50%, between about 40% and about 45%, and between about 40% and about 50%.

The amount of L-threonine or L-isoleucine, as well as other amino acids, present in culture media can be measured by a number of methods. For example, as indicated below in Examples 2 and 5, the amount of L-threonine, as well as other amino acids, present in culture media can be determined using HPLC. L-threonine or L-isoleucine levels can also be determined using methods such as paper chromatography with ninhydrin detection, thin layer chromatography, or microbiological assay.

C. Preparation of Bacterial Strains Capable of Over-Producing Amino Acids

As discussed above, bacterial strains well suited for commercial production of amino acids will generally be altered in more than one phenotypic trait related to production/excretion of the particular amino acids as compared to wild-type strains. As also discussed above, bacterial strains of the invention which over-produce amino acids include strains which contain at least one thr operon which (a) is integrated into the bacterial chromosome and (b) is under control of a non-native promoter. These strains will also generally contain phenotypic changes related to one, two, three, four, or more of the following: (1) the elimination or reduction of feed-back control mechanisms for one, two, three or more biosynthetic pathways which lead to production of amino acids or amino acid precursors; (2) the enhancement of metabolic flow by either amplification or increasing expression of genes which encode rate-limiting enzymes of biosynthetic pathways which lead to the production of amino acids (e.g., L-threonine or L-isoleucine) or amino acid precursors (e.g., aspartate); (3) the inhibition of degradation pathways involving either the desired amino acid end product (e.g., L-threonine or L-isoleucine), intermediates (e.g., homoserine), and/or precursors (e.g., aspartate); (4) increased production of intermediates and/or and precursors; (5) when the pathway which leads to production of a desired amino acid end product is branched, inhibition of branches which do not lead the desired end product or an intermediate and/or a precursor of the desired end product (e.g., inhibiting the E. coli methionine pathway, when the desired end product is L-threonine or L-isoleucine); (6) alterations in membrane permeability to optimize uptake of energy molecules (e.g., glucose), intermediates and/or precursors; (7) alterations in membrane permeability to optimize amino acid end product (e.g., L-threonine or L-isoleucine) excretion; (8) the enhancement of growth tolerance to relatively high concentrations of end products (e.g., amino acids), metabolic waste products (e.g., acetic acid), or metabolic side products (e.g., amino acid derivatives) which are inhibitory to bacterial cell growth; (9) the enhancement of resistance to high osmotic pressure during cultivation resulting from increased concentrations of carbon sources (e.g., glucose) or end products (e.g., amino acids); (10) the enhancement of growth tolerance to changes in environmental conditions (e.g., pressure, temperature, pH, etc.); and (11) increasing activities of enzymes involved in the uptake and use of carbon sources in the culture medium (e.g., raffinose, stachyose or proteins, as well as other components of corn steep liquor).

The invention also includes methods for screening bacterial cells to identify cells which have been subjected to mutagenesis and have one, two, three, four, or more of the characteristics set out above. Further included in the invention are bacterial strains which have one, two, three, four, or more of the above characteristics.

As one skilled in the art would recognize, the use of random mutagenesis, followed by screening to identify cells of the invention which over-produce a desired amino acid (e.g., L-threonine or L-isoleucine) results in the selection of cells having phenotypic changes that do not necessarily provide an indication of the mechanism by which the cell over-produces the amino acid. For example, amino acid over-production could be related to pleiotropic effect of an apparent unrelated phenotypic alteration. Thus, the invention is not limited to cells which over-produce amino acids and exhibit one or more of the metabolic alterations set out in the preceding list. In other words, the invention includes cells which are characterized by the ability to produce specified quantities of particular amino acids upon growth in culture for specified periods of time.

In specific embodiments, the strains of the invention are produced by subjecting bacterial cells containing at least one thr operon on the chromosome under the control of a non-native promoter to one, two, three, four, five, or more cycles of mutagenesis followed by screening to identify cells demonstrating increased production of amino acids (e.g., L-threonine or L-isoleucine).

A considerable number of methods for performing metagenesis are known in the art and can be used to generate bacterial strains of the invention. In general, these methods involve the use of chemical agents or radiation for inducing mutations.

Examples of classes of chemical compound used in mutagenic procedures are alkylating and ethylating agents, such as N-methyl-N-nitrosourea N-nitroso-N,N-diethylamine (NDEA) and N-ethyl-N'-nitro-N-nitrosoguanidine (ENNG), which have been known for some time to induce mutations in nucleic acid molecules (Hince et al., *Mutat. Res.* 46:1-10 (1977); J. Jia et al., *Mutat. Res.* 352:39-45 (1996)).

Intercalating agents, such as ethidium bromide, as well as other agents which bind to nucleic acid molecules, have also been shown to have mutagenic activity. For example, SYBR Green I stain, a non-intercalating nucleic acid stain, has been shown using the Ames test to induce mutations (Singer et al., *Mutat. Res.* 439:37-47 (1999)).

Other agents which can be used to induce mutations include, hydroxylamine, bisulfites, nitrofurans (e.g., 7-methoxy-2-nitronaphtho [2,1-p]furan (R7000)), and agents which induce oxidative stress (P. Quillardet et al., *Mutat. Res.* 358:113-122 (1996); G. Wang et al., *Mol. Gen. Genet.* 251:573-579 (1996)).

One skilled in the art would understand how to adjust the concentrations of the mutagenic agent and/or the particular conditions to achieve a desired mutation rate. For example, when ionizing radiation is used to produce mutagenized cells, the intensity of the radiation or duration of exposure can be adjusted to induce a particular number of mutations per cell. Further, the intensity of the radiation or duration of exposure can also be adjusted so that a particular percentage (e.g., 5%) of the treated cells survive.

After cells have been subjected to mutagenesis, they can be screened to determine whether they have particular characteristics. It is noted long these lines that a number of characteristics have been associated with increased production of L-threonine or L-isoleucine by bacterial cells. Example of such characteristics include resistance to cysteine, threonine, methionine, and purine analogs; resistance to isoleucine antagonists; impaired uptake of L-threonine uptake; and altered feedback inhibition of enzymes in the threonine and isoleucine biosynthetic pathways (see, e.g., Takano et al., U.S. Pat. No. 5,087,566; Yamada et al., U.S. Pat. No. 5,098,835; Yamada et al., U.S. Pat. No. 5,264,353; Kino et al., U.S. Pat. No. 5,474,918; K. Okamoto et al., *Biosci. Biotechnol. Biochem.* 61:1877-1882 (1997); Sahm et al., *Annals N.Y. Acad. Sci.* 782:25-39 (1996); Hashiguchi et al., *Biosci. Biotechnol. Biochem.* 63:672-679 (1999)). Other characteristics believed to correlate with increased production of L-threonine include resistance to L-threonine and TRF.

Further, screening/selection of cells having an L-threonine resistant phenotype may be done in media containing from about 1% to about 15% (weight/volume) L-threonine. For example, microorganisms of the invention can be screened using culture media containing about 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8%, 10%, 10.2%, 10.4%, 10.6%, 10.8%, 11%, 11.2%, 11.4%, 11.6%, 11.8%, 12%, 12.2%, 12.4%, 12.6%, 12.8%, 13%, 13.2%, 13.4%, 13.6%, 13.8%, 14%, 14.2%, 14.4%, 14.6%, 14.8%, 15%, 15.2%, 15.4%, 15.6%, 15.8%, or 16% L-threonine.

Strains of the invention may be generated by using multiple cycles of mutagenesis and screening. After each mutagenic treatment, the mutagenized cells can be screened for either (1) increased production of a desired amino acid end product (e.g., L-threonine or L-isoleucine) or (2) one, two, three, four, five, or more characteristics associated with increased production of the end product (e.g., L-threonine or L-isoleucine), followed by screening for increased production of the desired amino acid end product (e.g., L-threonine or L-isoleucine).

As noted above, one characteristic associated with increased threonine production is resistance to TRF. Thus, the invention includes bacterial strains which are resistant to TRF, as well as methods for producing and identifying TRF resistant mutants.

TRF can be prepared, for example, by protocols similar to the following. Particular matter is removed by ultrafiltration from conditioned threonine fermentation broth prepared, for example, as described below in Example 9 using fermentor fermentation medium. The permeate is then evaporated to concentrate threonine. Crystallized threonine is then recovered from the concentrated broth by centrifugation, using, for example, a continuous flow rotor. The liquid separated from the threonine is then processes through an ion exchange chromatographic separation system, such as C-SEP or I-SEP (Advanced Separation Technologies, Inc., St. Petersburg, Fla.). The waste effluent obtained therefrom is referred to as a "TRF" solution.

As one skilled in the art would recognize, separation methods other than C-SEP or I-SEP could also be employed. Ion exchange chromatographic separation systems are commonly known in the art, as exemplified in U.S. Pat. Nos. 4,808,317 and 4,764,276, which are incorporated herein by reference.

One TRF preparation prepared by the inventors was analyzed and found to contain the following components: aspartic acid (63 ppm), threonine (438 ppm), glutamic acid (24 ppm), proline (<14 ppm), glycine (40 ppm), alanine (16 ppm), cystine (42 ppm), valine (<18 ppm), methionine (232 ppm), isoleucine (297 ppm), leucine (25 ppm), tyrosine (31 ppm), phenylalanine (22 ppm), lysine (152 ppm), serine (<1 ppm), histidine (1 ppm), arginine (<22 ppm), ammonia (1,791 ppm), raffinose (5,036 ppm), sucrose (1,885 ppm), glucose (1,344 ppm), and fructose (725 ppm).

As can be seen from the above, TRF contains a considerable amount of ammonia sulfate, L-threonine, other amino acids, salts, and carbohydrates. Thus, TRF contains nitrogen sources, such as ammonia sulfate, and nutrients, such as amino acids and carbohydrates, which can be metabolized by microorganisms.

TRF concentration may be determined by determining the concentration of a reference component present in the TRF. One example of a reference component is ammonium sulfate. Unless otherwise stated herein, the concentration of a TRF solution is based on the percentage of ammonium sulfate present (wt./vol.). For example, a 5% TRF solution would contain 5 grams of ammonium sulfate per 100 milliliters of solute.

The ammonium sulfate concentration of a solution can be determined using a number of methods. For example, an ion selective probe can be used to measure the concentration of ammonium ions (e.g., ORION Research, Inc., 500 Cummings Center, Beverly, Mass. 01915, Catalog No. 931801).

When TRF is used to either (1) generate bacterial strains which over-produce L-threonine or (2) identify TRF resistant bacterial strains, the TRF will generally be prepared as described below in Example 10.

Raffinate solutions may be sterilized by any number of means prior to use in protocols for generating and screening raffinate resistant bacterial strains. The inventors have determined that sterilization of raffinate containing media, especially at high concentrations of solutes, using heat treatment produces amino acid derivatives and other metabolic antagonists which inhibit culture growth. However, heat sterilized TRF containing medium may be used to select mutants that are resistant to amino acid derivatives, especially L-threonine derivatives, through the improvement of their threonine production. To avoid alterations in raffinate properties associated with heat sterilization, culture media may be sterilized, for example, by ultrafiltration.

Strains of the invention include strains having an improved raffinate resistant phenotype, which is determined by the concentration of raffinate, as measured by ammonium sulfate content, in the selection medium employed. As discussed above, selection for raffinate resistant mutants may be done in a culture media containing raffinate. The particular concentration of raffinate present in the selection medium will vary with factors such as the medium itself, the cells being screened for raffinate resistance, and the raffinate preparation itself. For example, TRF resistant *E. coli* may be selected using minimal medium E (see Examples 6 and 7) containing from about 0.2% to about 0.5% raffinate. As one skilled in the art would understand, the TRF concentrations used will also vary with factors such as the genus and species of bacteria used and the initial sensitivity of the bacterial strain to TRF.

Bacterial strains of the invention may be made by performing mutagenesis on a parent bacterial strain followed by selection for cells exhibiting a TRF-resistant phenotype. Parent microorganisms may be selected from any organism useful for the fermentative production of amino acids (e.g., L-threonine); however, in most instances, the organism will be a strain of *E. coli*.

Screening/selection of cells having a TRF-resistant phenotype may be performed in culture media containing from about 0.05% to about 5% TRF. For example, microorganisms of the invention can be screened using culture media containing about 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.2%, 2.4%, 2.6%, 2.8%, 3.0%, 3.2%, 3.4%, 3.6%, 3.8%, 4.0%, 4.2%, 4.4%, 4.6%, 4.8%, or 5.0% TRF. As noted above, the TRF concentration is determined by with respect to the amount of ammonium sulfate present.

In one specific embodiment of the invention, *E. coli* strain 472T23, which requires threonine for growth, may be converted to a threonine producer using P1-mediated transduction to introduce the threonine operon of *E. coli* strain ATCC Deposit No. 21277, which may be obtained from the American Type Culture Collection, 10801 University Blvd., Manassas, Va. 20110-2209, USA. This thr operon composed of a feedback resistant aspartate kinase-homoserine dehydrogenase gene (thrA), a homoserine kinase gene (thrB), and a threonine synthase gene (thrC). This strain may then be subjected to one, two, three, four, or more cycles of mutagenesis, as described above, followed by screening to identify cells which produce increased quantities of L-threonine or L-isoleucine.

To increase threonine production, the defective threonine dehydrogenase gene from *E. coli* strain CGSC6945 (relevant genotype: tdh-1::cat1212; obtained from the *E. coli* Genetic Stock Center, 355 Osborne Memorial Laboratory, Department of Biology, Yale University, New Haven, Conn. 06520-8104, USA) may be introduced into the cells by P1 transduction. Again, the resulting threonine producer may be further improved by mutagenesis followed by the identification of cells which produce increased amounts of L-threonine or L-isoleucine.

Plasmids carrying an antibiotic resistance marker gene, such as kan (which encodes for kanomycin resistance), and a strong promoter, such as $P_L$ or tac, optionally flanked by DNA upstream of thrA and a few hundred base pairs of the wild-type thrA gene (i.e., not the whole thrA gene), may be constructed and used as a vehicle to deliver the desired DNA fragment into the chromosome. The DNA fragment may be isolated by digestion with a suitable restriction enzyme and purified, and then introduced, through transformation or electroporation, into a strain to remove the control region of threonine operon and replace it by homologous recombination with the desired fragment (e.g., a fragment containing an antibiotic resistance marker gene and a strong promoter at the beginning the thrA gene). This fragment may then be transferred into the cells of the strain by P1 transduction.

When increased production of L-threonine is desired, the isoleucine requirement of the strain of the one specific host, 472T23, may be eliminated, for example, by introducing a wild-type allele of the marker through P1 transduction. Unwanted nutritional requirements of other hosts may be removed in a similar manner or according to other methods known and available to those skilled in the art.

Borrelidin- or CPCA-resistant strains of the invention may contain one or more recombinant plasmids as desired. For example, the inventive microorganisms may contain recombinant plasmids that encode biosynthetic enzymes of the threonine pathway. The inventive bacterial strains may likewise contain recombinant plasmids encoding other enzymes involved in threonine biosynthesis, such as aspartate semialdehyde dehydrogenase (asd), or enzymes which augment growth.

Additionally, the Borrelidin- or CPCA-resistant strains may be modified as desired, for example, in order to increase threonine production, remove nutritional requirements, and the like, using any of the methods and techniques known and available to those skilled in the art. Illustrative examples of suitable methods for modifying Borrelidin- or CPCA-resistant *E. coli* mutants and variants include, but are not limited to: mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by transforming linear DNA fragments and homologous recombination; and transduction mediated by bacteriophages such as P1. These methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989).

The present invention also includes the use of borrelidin- or CPCA-resistant bacterial strains in fermentation processes for the production of L-threonine (e.g., borrelidin- or CPCA-resistant mutants of *E. coli*). Specific embodiments of the invention include mutant derivatives of *E. coli* strain ADM Kat13, which was deposited at the Agricultural Research Service Culture Collection (NRRL), 1815 North University Street, Peoria, Ill. 61604, USA, on Jun. 28, 1996 and assigned accession number NRRL B-21593 and is described in Wang et al., U.S. Pat. No. 5,939,307. Thus, strain ADM Kat13 may be subjected to one, two, three, four, or more cycles of mutagenesis, as described above, followed by screening to identify cells which produce increased quantities of L-threonine or L-isoleucine.

Borrelidin or CPCA resistance may be determined by any of the accepted methods known to those skilled in the art. For example, borrelidin- or CPCA-resistant strains can be isolated by plating the candidate strains on minimal medium containing about 139 μM borrelidin or CPCA, as described in G. Nass and J. Thomale, *FEBS Lett.* 39:182-186 (1974). In addition, borrelidin or CPCA resistance in certain strains is manifested as a change in one or more phenotypic characteristics of the cells. For example, borrelidin-resistant mutants of *E. coli* strain 6-8 and its derivatives appear round, rather than as rods. In such cases, evidence of a change in a phenotypic characteristic may be sufficient to adequately identify borrelidin-resistant strains.

The borrelidin- or CPCA-resistant mutants useful in this embodiment of the present invention are capable of producing threonine. The genes that encode the threonine biosynthetic enzymes may be present on the chromosome or contained in plasmids or mixtures thereof. Multiple copies of these genes may also be present. For example, the genes that encode the threonine biosynthetic enzymes may be resistant to attenuation control and/or encode feedback-resistant enzymes.

Further, borrelidin- or CPCA-resistant mutants may also be subjected to one or more cycle of mutagenesis, followed by screening to identify cells having desired characteristics, as described above. Thus, the invention also includes borrelidin- or CPCA-resistant mutants of *E. coli* which are also resistant to TRF.

In one embodiment, the borrelidin- or CPCA-resistant mutants of the present invention are modified so as to include a non-native promoter upstream from and in operable link with one or more of the genes that encode the threonine biosynthetic enzymes, regardless of whether these genes are on the chromosome and/or contained in plasmids.

D. Strains of the Invention

Examples of organisms, in addition to *E. coli*, which can be used to prepare strains of the invention which produce increased quantities of amino acids include *Brevibacterium flavum*, *Brevibacterium lactofermentum*, *Brevibacterium divaricatum*, *Brevibacterium saccharolyticum*, *Corynebacterium glutamicum*, *Corynebacterium acetoacidophilum*, *Corynebacterium lilium*, *Corynebacterium melassecola*, *Microbacterium ammoniaphilum*, and *Serratia marcesens*.

In many instances, the inventive bacterial strains are strains of *E. coli*. Further, as noted above, the invention includes bacterial strains (e.g., *E. coli* strains) which exhibit resistance to the macrolide antibiotic borrelidin or cyclopentanecarboxylic acid. Specific examples of bacterial strains of the invention include *E. coli* strains ADM Kat69.9 (NRRL B-30316), ADM TH14.97 (NRRL B-30317), ADM TH21.97 (NRRL B-30318), and ADM TH25.79 (NRRL B-30319), each of which were deposited at the Agricultural Research Service Culture Collection (NRRL), 1815 North University Street, Peoria, Ill. 61604, USA, on Jul. 27, 2000.

Strains of the invention also include strains which have the characteristics of the deposited strains assigned accession number NRRL B-30316, NRRL B-30317, NRRL B-30318, and NRRL B-30319. Particular characteristics these strains are set out below in Example 7.

Further included within the scope of the invention are bacterial strains that do not require any recombinant plasmids containing one, two or more genes that encode threonine biosynthetic enzymes for threonine production (i.e., strains capable of producing threonine without the need for one or more of the threonine biosynthetic enzymes to be encoded by genes contained in a recombinant plasmid).

The inventive strains may, of course, optionally contain recombinant plasmids as desired. For example, while such plasmids are generally not required for threonine production, the inventive strains may nevertheless contain recombinant plasmids that encode for threonine biosynthetic enzymes in order to increase threonine production. The inventive strains may likewise contain recombinant plasmids encoding other enzymes involved in threonine biosynthesis, such as aspartate semialdehyde dehydrogenase (asd).

Strains of the invention also include strains which are resistant to TRF and other agents resistance to which correlates with increased threonine production (e.g., cysteine, threonine and methionine analogs; isoleucine antagonists; and purine analogues).

In certain embodiments, the strains of the invention do not include one or more of the following strains of *E. coli*: KY10935, ADM TH1.2, BKIIM B-3996, H-8460, ADM Kat13, tac3,6-8, 6-8tac3, and 6-8tac3ile+. In other embodiments, the strains of the invention do not include *Serratia marcescens* strain T2000.

In many instances, the novel bacterial strains also have no amino acid nutritional requirements for fermentative production of threonine (i.e., the cells do not require amino acids supplements for growth and threonine production). Alternatively, bacterial strains of the invention may require methionine or isoleucine for growth.

III. USE OF THE STRAINS OF THE INVENTION TO PRODUCE AMINO ACIDS

The present invention is also directed to the use of the above-described bacterial strains in fermentation processes for the production of amino acids, amino acids of the aspartate family in particular. L-threonine and L-isoleucine, for examples, may be obtained by culturing the inventive bacterial strains in a synthetic or natural medium containing at least one carbon source, at least one nitrogen source and, as appropriate, inorganic salts, growth factors and the like.

Illustrative examples of suitable carbon sources include, but are not limited to: carbohydrates, such as dextrose, fructose, sucrose, starch hydrolysate, cellulose hydrolysate and molasses; organic acids, such as acetic acid, propionic acid, formic acid, malic acid, citric acid, and fumaric acid; and alcohols, such as glycerol and ethanol.

Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing, including meat extract, peptone, corn steep liquor, casein hydrolysate, soybean cake hydrolysate and yeast extract.

Culture media suitable for use with the present invention include the following:
1. Minimal Medium E (described below in Example 1).
2. Yeast extract 2 g/L, citric acid 2 g/L, $(NH_4)_2SO_4$ 25 g/L, $KH_2PO_4$ 7.46 g/L, $CaCO_3$ 20 g/L, dextrose 40 g/L, and $MgSO_4\cdot 7H_2O$ 2 g/L, supplemented with trace metals, pH 7.2.
3. Yeast extract 5 g/L and tryptic soy broth 30 g/L.

Amino acids may be commercially produced using strains of the invention in, for example, batch type or fed-batch type fermentation processes. In batch type fermentations, all nutrients are added at the beginning of the fermentation. In fed-batch or extended fed-batch type fermentations one or more nutrients are supplied (1) continuously to the culture, (2) right from the beginning of the fermentation or after the culture has reached a certain age, or (3) when the nutrient(s) which are fed are exhausted from the culture medium.

A variation of the extended batch of fed-batch type fermentation is the repeated fed-batch or fill-and-draw fermentation, where part of the contents of the fermentor is removed at a particular time (e.g., when the fermentor is full) while feeding of a nutrient is continued. In this way a fermentation can be extended for a longer time as compared to when such methods are not used.

Another type of fermentation, the continuous fermentation or chemostat culture, uses continuous feeding of a complete medium, while culture fluid is continuously or semi-continuously withdrawn in such a way that the volume of the broth in the fermentor remains approximately constant. A continuous fermentation can in principle be maintained for an infinite period of time.

In a batch fermentation, the cultured organism grows until either one of the essential nutrients in the medium becomes exhausted or fermentation conditions become unfavorable (e.g., the pH decreases to a value inhibitory for microbial growth). In fed-batch fermentations measures are normally taken to maintain favorable growth conditions (e.g., by using pH control) and exhaustion of one or more essential nutrients is prevented by feeding these nutrient(s) to the culture. Thus, the cultured microorganism will normally continue to grow at a rate determined by the rate of nutrient feed.

In most instances, a single nutrient, very often the carbon source, will become limiting for growth. The same principle applies during continuous fermentation, usually one nutrient in the medium feed is limiting and all of the other nutrients are in excess. After the microorganisms have stopped growing, the limiting nutrient will generally be present in the culture fluid in an extremely low concentration.

While different types of nutrient limitation can be employed, carbon source limitation is used most often. Other examples are limiting nutrients include the nitrogen, sulfur, phosphorous, trace metal, and oxygen sources. Vitamins and amino acid (in cases where the microorganism being cultured is auxotrophic for the limiting amino acid) can also be limiting nutrients.

After cultivation, amino acids (e.g., L-threonine or L-isoleucine) that have accumulated in the culture broth can be separated according to a variety of methods. For example, ion-exchange resins according to purify L-threonine according to methods described in U.S. Pat. No. 5,342,766. This method involves first removing the microorganisms from the culture broth by centrifugation and then adjusting the pH of the broth to about 2 using hydrochloric acid. The acidified solution is subsequently passed through a strongly acidic cation exchange resin and the adsorbent eluted using dilute aqueous ammonia. The ammonia is removed by evaporation under vacuum, and the resulting solution is condensed. Addition of alcohol and subsequent cooling provides crystals of L-threonine. As similar method for the purification of L-isoleucine from culture media is described in U.S. Pat. No. 5,474,918.

Other amino acids of the aspartate family can be produced by methods similar to those described above. Isoleucine, for example, can be prepared from the inventive bacterial strains containing, on the chromosome or on a plasmid, an amplified ilvA gene or tdc gene, both of which encode threonine deaminase, the first enzyme involved in the bioconversion of threonine to isoleucine. Amplification of this gene, for example, by use of a ilvA gene encoding a feedback-resistant enzyme, leads to increased biosynthesis of isoleucine.

Similarly, methionine can be prepared by microorganisms such as E. coli that contain at least one met operon on the chromosome (i.e., the metL gene (which encodes AK II-HD II), the metA gene (homoserine succinyltransferase), the metB gene (cystathionine γ-synthase), the metC gene (cystathionine β-lyase), and the metE and metH genes (homocysteine methylase)). These genes, including feedback-resistant variants thereof, and, optionally, a non-native promoter can be introduced into the chromosome of the host microorganism according to general methods discussed above and/or known to those skilled in the art. Lysine can likewise be prepared by microorganisms that contain a gene encoding the lysine biosynthetic enzymes (e.g., a feedback-resistant lysine biosynthetic enzyme encoded by lysC and/or dapA) and, optionally, a non-native promoter.

The present invention also includes the use of borrelidin- or CPCA-resistant bacterial strains in fermentation processes for the production of L-threonine (e.g., borrelidin- or CPCA-resistant mutants of E. coli).

In specific embodiments of the present invention, L-threonine or L-isoleucine is obtained by culturing borrelidin- or CPCA-resistant microorganisms in a synthetic or natural medium containing at least one carbon source, at least one nitrogen source and, as appropriate, inorganic salts, growth factors and the like, as described above. Amino acids which accumulate in the culture media can be recovered by any of the methods known to those skilled in the art.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

Example 1

Preparation of E. coli Strain ADM Kat13

A. Transfer of the Threonine Operon of E. coli Strain ATCC Deposit No. 21277 into the Chromosome of E. coli Strain 472T23.

E. coli strain ATCC Deposit No. 21277 (U.S. Pat. No. 3,580,810), available from the American Type Culture Collection, 10801 University Blvd., Manassas, Va. 20110-2209, USA, is amino-β-hydroxyvaleric acid (AHV) resistant but requires proline, thiamine, isoleucine, and methionine to grow in a minimal medium. ATCC Deposit No. 21277 is reported to accumulate 6.20 g/L of threonine in a fermentation process. The threonine operon of ATCC Deposit No. 21277 is composed of an aspartate kinase I-homoserine dehydrogenase I gene (thrA) that encodes a feedback-resistant enzyme, a homoserine kinase gene (thrB), and a threonine synthase gene (thrC).

E. coli strain 472T23, which is deposited in the USSR Collection of Commercial Microorganisms at USSR Antibiotics Research Institute under Reg. No. BKIIM B-2307, is reported to require threonine and isoleucine and to grow in a minimal medium which contains glucose, ammonia, vitamin B1, and mineral salts. This strain cannot produce threonine because it carries a defective thrC gene, an essential gene for threonine biosynthesis. The strain 472T23 also carries a defective threonine deaminase gene, ilvA, which codes for the first enzyme in isoleucine biosynthesis.

Bacteriophage P1 lysate was prepared by growing phage on ATCC Deposit No. 21277. Strain 472T23 was then infected with this P1 lysate, in which a smaller number of the phage particles carried the threonine operon of ATCC Deposit No. 21277. Following infection, bacterial synthesizing threonine were selected by spreading on minimal medium E (glucose 0.05 g/L; $MgSO_4$ $7H_2O$ 0.2 g/L; citric acid $H_2O$ 2.0 g/L; $K_2HPO_4$ 10.0 g/L; $NaHNH_4PO_4$ $4H_2O$ 3.5 g/L; agar 15.0 g/L) agar plates supplemented with 0.25 g/L isoleucine. Several threonine prototrophic transductants, which carried the threonine operon of ATCC Deposit No. 21277, were now able to grow in a minimal plates supplemented only with isoleucine.

These tranductants were screened by shake-flask fermentation for threonine production as described below in Example 2. One of them, G9, producing threonine, was selected for further strain development.

B. Transfer of a Defective Threonine Dehydrogenase (tdh) Gene Inserted with a Chloramphenicol Acetyltransferase (cat) Gene into the Chromosome of E. coli Strain G9.

Strain CGSC6945, carrying a defective threonine dehydrogenase gene (tdh), was obtained from the E. coli Genetic Stock Center, 355 Osborne Memorial Laboratory, Department of Biology, Yale University, New Haven, Conn. 06520-8104, USA. The threonine dehydrogenase gene is defective because inserted into it is the chloramphenicol acetyltransferase (cat) gene. To transfer this defective gene to G9, P1 phase were grown on CSCG6945, and the lysate was used to infect G9. Several chloramphenicol-resistant transductants of G9 were selected and screened for threonine production with shake-flask fermentation as described below in Example 2. One of them, G909, with a higher threonine titer than G9, was selected for further development.

C. Insertion of a Non-Native Promoter into the Chromosome of E. coli Strain G. 909

In order to deliver the tac promoter into the chromosome of G909, homologous recombination between a linear DNA fragment and the chromosome of an exonuclease V minus strain (recD) was employed.

The linear DNA fragment contained 1.5 kb of the sequence upstream (5' end) of the threonine operon, a kanamycin resistant marker, the tac promoter sequence, and about 480 bp of the thrA gene. This fragment, which provided 5' end homology, a selection marker (kanamycin resistance), a strong and controllable promoter to the threonine operon (tac), and 3' end homology, respectively, was generated as follows.

The threonine operon of the wild-type E. coli W3110 was cloned into the restriction enzyme SphI site of plasmid pUC19 by using the DNA of the lambda clone 676 from Dr. Yuji Kohara, Department of Molecular Biology, School of Science, Nagoya University, Chikusa-ku, Nagoya, Japan. The DNAs of lambda clone 676 and pUC19 were then digested with SphI. The pUC19 fragment was subsequently dephosphorylated with shrimp alkaline phosphatase (SAP) and agarose-gel purified. The 6.9 kb fragment of threonine operon from lambda clone was also purified. These two fragments were subsequently ligated by T4 DNA ligase to generate plasmid pAD103.

An upstream flanking region for homologous recombination and kanamycin resistance marker was then constructed. pAD103 was digested with restriction enzyme BstEII, XbaI and blunt-ended with klenow fragment treatment. The 1.5 kb fragment containing only the 5' end (upstream) of the threonine operon (but not the thr operon itself or its control region) was isolated and ligated to the fragment of kanamycin resistance gene from pUC4K (Pharmacia), which was digested with restriction enzyme SalI and klenow fragment treated to fill-in the 3' overhangs to generate intermediate plasmid pAD106. pAD103 was also digested with restriction enzyme TaqI and blunt-ended with klenow fragment treatment. The fragment containing the native ribosome binding site and about 480 bp of the coding sequence of the thrA gene was isolated and then ligated to a fragment of pKK233-3 (Pharmacia), which had been digested with restriction enzyme SmaI and dephosphorylated with SAP, to obtain plasmid pAD115, which contained the DNA sequence of the tac promoter, the ribosome binding sites and a few hundred bases of the thrA gene.

pAD115 was subsequently digested with restriction enzyme BamHI and 0.75 kb of the DNA fragment which contained the desired DNA sequences was isolated. pAD106 was also digested with BamHI and then dephosphorylated with SAP. The two fragments were then ligated to provide plasmid pAD123, which contained the DNA sequence upstream of the threonine operon, a kanamycin resistance marker gene, the tac promoter, and about 480 bp of the beginning of the thrA gene.

pAD123 was then digested with SpeI, BglI and the fragment containing the desired DNA sequences was isolated.

The exonuclease V minus strain (recD) was prepared by growing P1 phage on E. coli strain KW251 (relevant genotype: argA81::Tn10, recD1014, obtained from Pharmacia), which contains a recD gene with a co-transducible transposon Tn10 insertion in argA. The lysate which was prepared from the phage was then used to infect strain G9 and the tetracycline-resistant transductant G9T7 was isolated.

The DNA fragment from plasmid pAD123 was delivered to E. coli strain G9T7 by electroporation. A kanamycin-resistant strain of G9T7 was isolated and a P1 phage lysate was made by growing phage on this strain. The P1 phage lysate was then used to transduce G909. One of the kanamycin-resistant transductants of G909, tac3, which showed a higher threonine titer in the presence of IPTG in shake-flask study, was isolated.

P1 phage lysate was subsequently prepared with strain tac3 and then used to infect strain 6-8 (described below). The kanamycin-resistant transductants were selected and one of them, strain 6-8tac3, which produced an even higher titer than tac 3 in a shake-flask study, was isolated.

D. NTG Mutagenesis and the Isolation of Borrelidin-Resistant Mutants from E. coli Strains G909 and 6-8.

The cells of strain G909 were mutagenized by N-methyl-N'-nitro-N-nitrosoguanidine (NTG) treatment (50 mg/L, 30 min. at 36° C.) using conventional methods. The resulting cells were then spread on minimal medium E agar plate containing 0.25 g/L of L-isoleucine and 0.1% v/v of CPCA. After incubation for 3-5 days at 36° C., the large colonies that formed on the plate, which included strain 6-6, were selected for testing for CPCA resistance and L-threonine production.

To test for CPCA resistance, each strain was cultivated in 20 ml of the seed medium SM (32.5 g/L glucose; 1 g/L MgSO$_4$ 7H$_2$O; 24.36 g/L K$_2$HPO$_4$; 9.52 g/L KH$_2$PO$_4$; 5 g/L (NH$_4$)$_2$SO$_4$; 15 g/L yeast extract; pH 7.2) at 36° C. for 17 hr with shaking. The cells were harvested and washed with minimal medium E. The cell suspension was then inoculated into a sterilized tube containing 3 ml of minimal medium E and 0, 0.1, 0.5, or 1 mM CPCA. After 24 hr cultivation as 36° C. with shaking, growth was determined by measuring the optical density at 660 nm. The results are shown below in Table 1 relative to growth in the absence of CPCA.

TABLE 1

| CPCA (mM) | G909 | 6-8 |
|---|---|---|
| 0 | 100.0 | 100.0 |
| 0.1 | 24.2 | 134.5 |
| 0.5 | 2.9 | 141.0 |
| 1 | 0.9 | 184.5 |

E. Removal of Isoleucine Requirement and Lactose Repressor Gene (lacI).

By introducing the non-native tac promoter and a feedback-resistant thrA gene, expression of the thr operon (thrA, thrB, thrC) is no longer controlled by the attenuation mechanism. As a result, starvation for isoleucine and/or the presence of an ilvA auxotrophic marker is no longer required for threonine production.

Accordingly, the wild-type ilvA marker was introduced by transduction into 6-8tac3 to fix the isoleucine requirement of the strain (i.e., to eliminate the need for isoleucine-supplemented medium for cell growth). P1 phage lysate made from CGSC7334 (relevant genotype: lac142::Tn10, lacZU118; obtained from the *E. coli* Genetic stock Center, 355 Osborne Memorial Laboratory, Department of Biology, Yale University, New Haven, Conn. 06520-8104, USA) was used to infect 6-8tac3 and transductants positive for isoleucine biosynthesis were selected. These transductants produced approximately the same amount of L-threonine strain 6-8tac3 in a shake-flask study. One of these transductants, 6-8tac3ile+ was selected for further development.

Since the threonine operon of 6-8tac3ile is under the control of the tac promoter, isopropyl-β-D-thiogalactoside (IPTG) was necessary to induce the cells to fully express the thr operon.

Accordingly, to eliminate this unnecessary regulatory hindrance, a defective lac repressor (lacI) gene is introduced by infecting 6-8tac3ile+ with P1 phage made from CGSC7334. The resultant transductants (6-8tac3lacI−) were tested for resistance to tetracycline and tetracycline-resistant colonies were selected.

Example 2

Shake-Flask Fermentation Study of Threonine Production

A comparison of threonine production among the various *E. coli* strains was determined by their performance in shake-flask fermentation. The strains being tested were grown on LB agar medium (10 g/L of tryptone, 5 g/L of extract, 15 g/L agar). After 1 to 2 days of growth, the cells were suspended in 5 ml of seed medium (dextrose 3.25 g/L; K$_2$HPO$_4$ 24.35 g/L; KH$_2$PO$_4$ 9.5 g/L; yeast extract 15 g/L; (NH$_4$)SO$_4$ 5 g/L; MgSO$_4$ 7H$_2$O 1 g/L) at pH 7.2. The seed was grown for 24 hours with a stirring speed of 250 rpm at 37° C. 15 ml of fermentation medium (dextrose 40 g/L; yeast extract 2 g/L; citric acid 2 g/L; (NH$_4$)$_2$SO$_4$ 25 g/L; MgSO$_4$ 7H$_2$O 2.8 g/L; CaCO$_3$ 20 g/L; trace metal solution 2 ml) at pH 7.2 was then added to the seed and the fermentation process performed at 37° C. with a stirring speed of 250 rpm. After cultivation, the amount of L-threonine that had accumulated in the culture broth was analyzed by HPLC (ISCO Model 2353 pump, Rainin Model RI-1 refractive index detector, and aminex Hp87-CA column).

The amount of L-threonine produced by each of the tested strains is presented in Table 2 below.

TABLE 2

| Strain | L-Threonine Produced (g/L) |
|---|---|
| G909 | 4.95 |
| 6-8 | 11.45 |
| tac3 | 12.9 (induced by IPTG) |
|  | 10.6 (non-induced) |
| 6-8 tac3 ile+ | 12.7 (induced by IPTG) |
| 6-8 tac3 lacI− | 13.9 |
| ADM Kat13 | 14.0 |

Example 3

Fermentation Study

The *E. coli* strains of the present invention and their precursor strains were tested for L-threonine production by fermentation.

G909 was tested under the following conditions. 0.5 L of aqueous culture medium containing 30 g/L of tryptic soy broth and 5 g/L of yeast extract in a 2 L baffled shake flask was inoculated with 1.5 ml of G909 and incubated on shaker at 35° C. and 200 rpm for 8.5 hours. 0.9 ml (0.03%) of the mature inoculum was added to a glass fermentator containing 3.0 L of the seed fermentor medium (10 g/L d.s of corn steep liquor, 0.4 g/L of L-isoleucine, 2.5 g/L of KH$_2$PO$_4$, 2.0 g/L of MgSO$_4$ 7H$_2$O, 0.5 g/L of (H$_4$)$_2$SO$_4$, 0.192 g/L of anhydrous citric acid, 0.03 g/L of FeSO$_4$ 7H$_2$O, 0.021 g/L of MnSO$_4$H$_2$O and 80 g/L of dextrose). Incubation was conducted under the following conditions: a temperature of 39° C. for the first 18 hours, and then 37° C. for the duration; pH of 6.9 (maintained by addition of NH$_4$OH); air flow of 3.5 LPM; agitation of 500 rpm initially, which was then increased to maintain the D.O. at 20%; and back pressure of 1-2 psi. Completion of the seed fermentor stage was determined by depletion of dextrose. 315 ml (15%) of the mature inoculum from the seed fermentor was added to a glass fermentor containing the same medium (main fermentor medium) listed above with the following exceptions: volume was 2.1 L and 0.34 g/L of L-isoleucine was added. Incubation was conducted for 48 hours under the following conditions: temperature of 37° C.; pH of 6.9 (maintained with NH$_4$OH); air flow of 3.5 LPM until 20 hours then increased to 4.0 LPM; agitation of 500 rpm initially, which was then increased to maintain the D.O. at 20%; back pressure of 1-2 psi; and dextrose level of 10 g/L (maintained by feeding with a 50% w/w dextrose solution). The fermentation was terminated after 48 hours. G909 produced the following results: a final titer of 62.3 g/L of threonine with a total productivity of 274 g and a yield of 23.2%.

tac3 was tested under the same conditions as described above for G909 with the following exception: 1 mg/L of IPTG was added at the start of the main fermentor stage. With addition of IPTG, tac3 produced a final titer of 85.7 g/L of threonine with a total productivity of 355 g and a yield of 28.8%.

6-8 was tested under the same conditions as G909 described above. 6-8 produced the following results: a final titer of 74.1 g/L threonine with a total productivity of 290 g and a yield of 28.3%.

6-8tac3 was tested under the same conditions as tac3 described above, including the addition of IPTG. 6-8tac3 produced the following results: a final titer of 99.3 g/L threonine with a total productivity of 421 g and a yield of 35.1%.

6-8tac3ile+ was tested under the same conditions as 6-8tac3 as described above, with the following exception: no L-isoleucine was required in either the seed fermentor stage or the main fermentor stage. Due to an agitation failure at 22.5 hours, only the titer at 22 hours was recorded (62 g/L threonine).

ADM Kat13 was tested under the same conditions as 6-8tac3 as described above with the following exception: no IPTG was added. Under these conditions, ADM Kat13 produced a final titer of 102 g/L threonine with a total productivity of 445 g and a yield of 33.1%.

The relevant genotypes of the constructed strains, supplements required for fermentative production of threonine, and the titers recorded are presented in Table 3.

TABLE 3

| Strain | Relevant Genotype | Supplements for Production | Titer at 30 Hours | Titer at 48 Hours | Yield |
|---|---|---|---|---|---|
| G9 | ilvA; | Ile | ND | ND | ND |
| G909 | ilvA; tdh::Cm | Ile | 53 | 62.3 | 23.2 |
| tac3 | ilvA; tdh::Cm, ptacthrABC | Ile, IPTG | 86 | 85.7 | 28.8 |
| 6-8 | ilvA; tdh::Cm, Bor-R | Ile | 70 | 74.1 | 28.3 |
| 6-8tac3 | ilvA; tdh::Cm, ptacthrABC, Bor-R | Ile, IPTG | 75 | 99.3 | 35.1 |
| 6-8tac3ile+ | tdh::Cm, Bor-R, ptacthrABC | IPTG | 62 (at 22 hours) | NA | NA |
| ADM Kat13 | tdh::Cm, Bor-R, ptacthrABC lacI | None | 92.1 | 102 | 33.1 |

Bor-R: borrelidin Resistance
ND: Not done
NA: Not available
ptacthrABC: the thrA and the thrC genes under control of the tac promoter Example 4

Preparation of E. coli Strain ADM Kat69.9

A. Transfer of the Threonine Operon from an E. coli Strain, ADM Kat26, into the Chromosome of E. coli Strain W3110

Strain ADM Kat26 has been constructed previously from E. coli ATCC Deposit No. 21277 as shown in Table 4. The native threonine promoter of this strain has been replaced by the tac promoter, at the same time a kanamycin gene was introduced into the chromosome. A P1 lysate was prepared by growing phage on ADM Kat26. Strain W3110 (ATCC Deposit No. 27325) was infected with this lysate, in which a small number of the phage particles carried the threonine operon of ADM Kat26. Following infection, transfer of the threonine operon was selected for on rich media containing kanamycin. Several of these transductants were screened in shake flask fermentation for threonine production, and inducibility of the threonine operon. One of the transductants, ADM Kat60.6, was selected for further strain development.

B. Transfer of a Defective Threonine Dehydrogenase (tdh) Gene Inserted with Chloramphenical Acetyltransferase (cat) Gene and an Additional Copy of the Threonine Operon Under the Control of the tac Promoter into the Chromosome of E. coli Strain ADM Kat60.6

Figure 6:
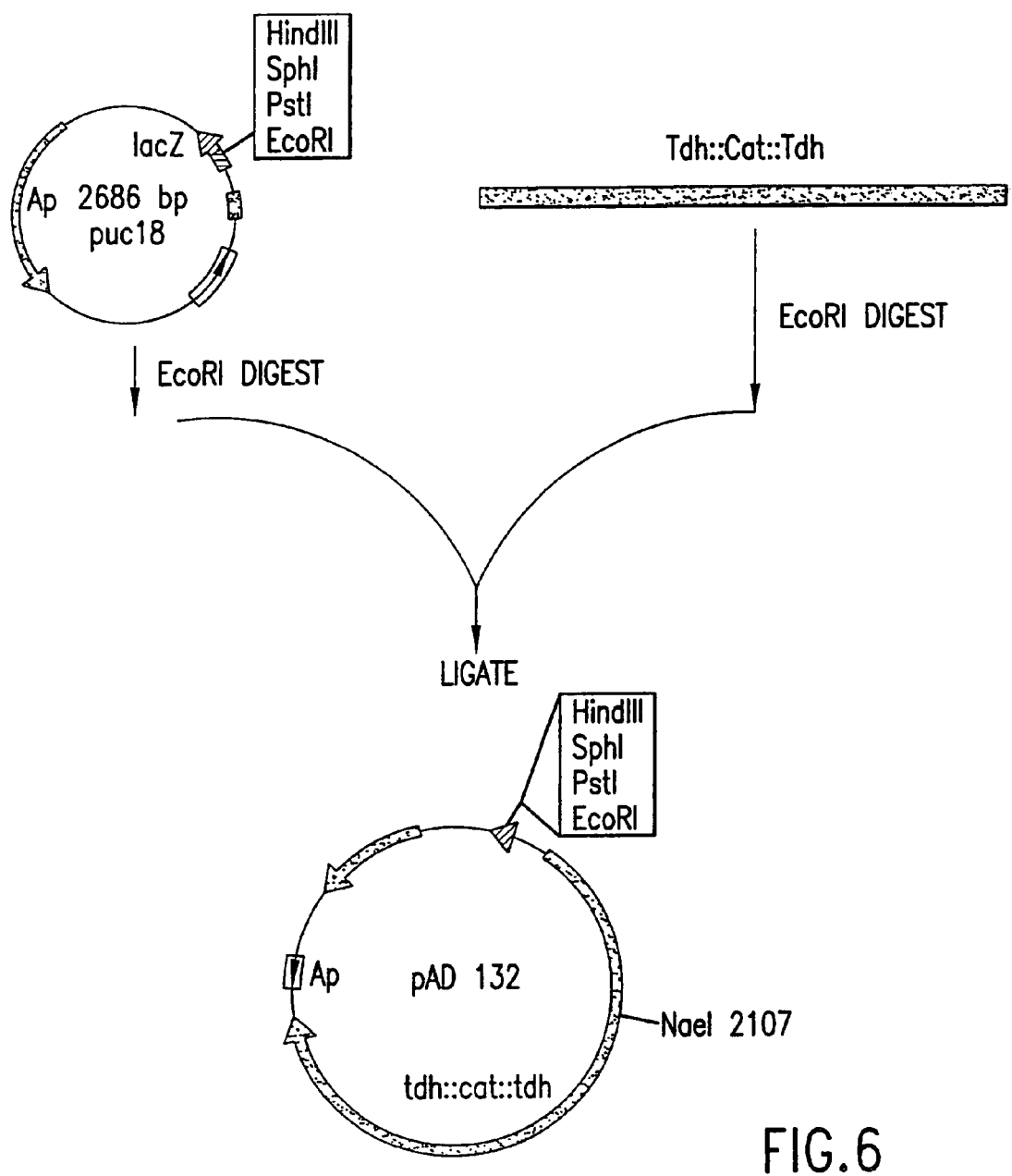
FIG. 6 depicts the construction of plasmid pAD132 by the insertion of the tdh::cat deletion from E. coli strain SP942 into plasmid pUC18.
Figure 7:
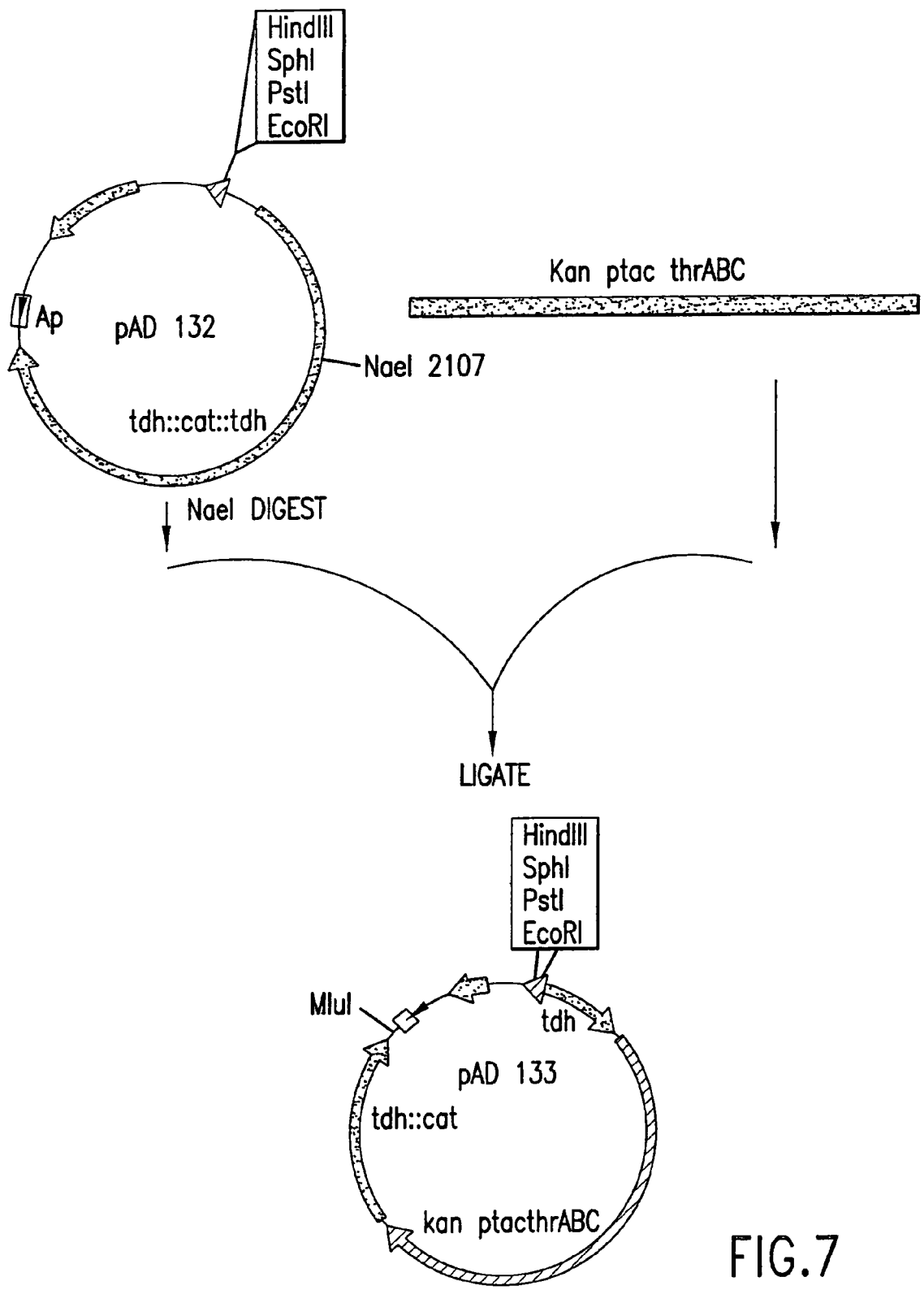
FIG. 7 depicts the construction of plasmid pAD133 by the insertion of nucleic acid containing a kanamycin resistance gene and a thr operon operably linked to a tac promoter into plasmid pAD132.

In order to introduce a second copy of the threonine operon into the chromosome, a vector was constructed which knocked out the tdh gene by inserting a copy of the threonine operon. The first step in this process was to construct a vector containing the appropriate genes. The tdh::cat deletion from strain SP942 was cloned by digesting genomic DNA with EcoRI, isolating the region of approximately 4.8 kb, and cloning into the EcoRI site of plasmid puc18 (FIG. 6). This plasmid was then digested with NaeI and the threonine operon with the kanamycin gene and tac promoter was cloned into the tdh gene (FIG. 7). This new construct was linearized by digest with MluI and HindIII restriction enzymes. The linear piece containing the tdh with the second copy of the thr operon was electroporated into a recD strain. Transformations were selected on rich media containing chloramphenical. A P1 lysate was made from one of these transformants, and was used to infect ADM Kat41, an ATCC Deposit No. 21277 derived threonine producer. A lysate was made from this train, and this lysate was used to infect ADM Kat60.6. The transductants were selected on rich media containing chloramphenical. Shake flask studies were performed to screen for the best producer. One strain, ADM Kat68, was chosen for further manipulations.

C. Removal of the Lactose Repressor Gene (lacI)

Since both threonine operons of ADM Kat68 are under the control of the tac promoter, isopropyl-B-D-thiogalactoside (IPTG) was necessary to induce the cells to fully express the thr operon. The use of IPTG to induce expression of the thr operon is less preferred. To eliminate this problem, a defective lac repressor (lacI) gene was introduced by infecting ADM Kat68 with P1 phage made from CAG 18439. All strains involved in the construction of ADM Kat69.9 (NRRL B-30316) and their genotypes were shown in Table 4. The resultant transductants were selected on rich media containing tetracycline, and then screened in shake flask for equal production of threonine with or without IPTG.

TABLE 4

| | |
|---|---|
| W3110 | F mrcA mcrB IN(rrnD-rrnE)1 lambda |
| ATCC 21277 | pro, thi, iso, met |
| SP942 | F, tdh-1::cat1212, IN(rrn-rrnE)1 |
| CAG 18439 | LacI/Tn10, lacZU118 |
| ADM Kat26 | kan-ptac-thrABC from tac3 transduced into Kat17 (ATCC 21277 pro+, met+) |
| ADM Kat41 | Kat36.36 (ATCC 2177 pro+, met+ w.kan-ptac-thrABC from tac3; w.tdh-cm-ptac-thrABC, lacI::Tn10 from pIvir from Kat13) with homoserine resistance from Kat 13 |
| ADM Kat60.6 | W3110 with kan-ptac-thrABC transduced from Kat26 |
| ADM Kat68 | Kat60.6 with tdh-cm-ptac-thrABC from Kat41 |
| ADM Kat69.9 | Kat68 with LacI::Tn10 |

Example 5

Shake-Flask Fermentation Study of Threonine Production

A comparison of various E. coli strains was performed using their production of threonine in the shake flask fermentation. The strains were grown on LB agar media overnight, and then transferred to 20 mls of shake flask media (dextrose 32.5 g/L; $K_2HPO_4$ 24.35 g/L; $KH_2PO_4$ 9.5 g/L; yeast extract 15 g/L; $(NH_4)_2SO_4$ 5 g/L, $MgSO_4$ $7H_2O$ 1 g/L) at pH 7.2. The seed was grown for 24 hours with a stirring speed of 300 rpm at 37° C. 2 ml of this cultured was transferred to the fermentation media (yeast extract 2 g/L; citric acid 2 g/L; $(NH_4)_2SO_4$ 25 g/L, $KH_2PO_4$ 7.46 g/L; trace metal solution 2 ml/L; $CaCO_3$ 20 g/L; Dextrose 40 g/L; $MgSO_4$ $7H_2O$ 2 g/L) at pH 7.2. The fermentation was then run for 24 hours at 37° C. and 300 rpm on a shaker. After cultivation, the amount of threonine accumulated in the broth was analyzed by HPLC (as shown in Table 5).

TABLE 5

| Strain | Threonine (g/L) | Yield % |
| --- | --- | --- |
| ADM Kat60.6 | 4 | 14 |
| ADM Kat68 | 7.5 | 19 |
| ADM Kat69.9 | 7.5 | 19 |

Example 6

Mutagenesis and Selection for Mutants with Improved L-Threonine Production from Strain ADM Kat69.9

The cells of strain ADM Kat69.9 (NRRL B-30316) or its mutants were harvested from mid-log phase cultures grown in LB, and then mutagenized with N-methyl-N' nitro-N-nitrosoguanidine (NTG) treatment (50 mg/L, 36° C., 25 minutes) in 3 ml of TM buffer (Tris HCl 6.0 g/L, maleic acid 5.8 g/L, $(NH_4)_2SO_4$ 1.0 g/L, $Ca(NO_3)_2$ 5 mg/L, $MgSO_4$ $7H_2O$ 0.1 g/L, $FeSO_4$ $7H_2O$ 0.25 mg/L, adjusted to pH 6.0 using KOH). After 25 minutes of reaction, the NTG treated cells were pelleted by centrifugation. The treated cells were washed twice in TM buffer and spread on minimal medium E (glucose 0.05 g/L, $MgSO_4$ $7H_2O$ 0.2 g/L, citric acid $H_2O$ 2.0 g/L, $K_2HPO_4$ 10.0 g/L, $Na(HN_4)PO_4$ $4H_2O$ 3.5 g/L) agar plates containing 4-8% of threonine or 0.2-0.5% of threonine raffinate (TRF) based on grams of ammonia sulfate per liter of medium, as determined using an ion sensitive probe which measures ammonium ions.

Figure 8:
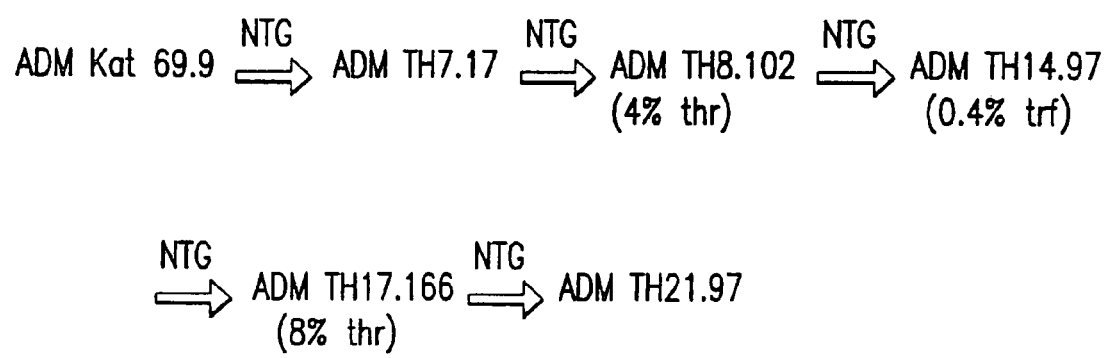
FIG. 8 depicts one specific embodiment of the stepwise mutagenic process described in Example 6 to generate strains of the invention which demonstrate improved production of L-threonine.

After incubation for 3-5 days at 36° C., colonies growing on these plates were picked and tested for improved L-threonine production in shaker flasks and fermentors. Mutants with improved threonine production were subjected to the next cycle of mutagenesis and selection. As shown in FIG. 8, strain ADM TH21.97 (NRRL B-30318) was developed from ADM Kat69.9 (NRRL B-30316) through the use of selection criterion designed to identify cells could grow faster, produce more L-threonine in the formulated fermentation medium, and tolerate higher concentrations of L-threonine and TRF as compared to their parent strains.

Example 7

Selection of Threonine Raffinate Mutants Strains

Both ADM TH14.97 (NRRL B-30317) and ADM TH25.79 (NRRL B-30319) are mutants which have been selected from E medium agar plates containing 0.2-0.4% of TRF as described in Example 6. Strain ADM TH14.97 is a TRF mutant of ADM TH8.102 developed from ADM Kat69.9 (NRRL B-30316) as described in FIG. 8. And strain ADM TH25.79 (NRRL B-30319) is a TRF mutant of ADM TH1.2 which was developed from ADM Kat13 (NRRL B-21593, U.S. Pat. No. 5,939,307). To study the effect of TRF on culture growth, selected TRF mutants and their parent strains were grown in media containing TRF. About 0.1 ml culture prepared from each tested strains was inoculated to a 250 ml baffled shaker flask containing 20 ml minimal medium E and TRF at 0.1-0.4% based on grams of ammonia sulfate per liter of medium. After shaking at 37° C. and 240 rpm for 24 hours, their growth O.D. was measured at 660 nm. As shown in Table 6, ADM TH14.97 and ADM TH25.79 grew better with higher O.D. in minimal medium E containing TRF than their respective parent strains ADM TH8.102 and ADM TH1.2.

TABLE 6

| | O.D. at 660 nm after growth in minimal medium E at 37° C. and 240 rpm for 24 hours. | | | |
| --- | --- | --- | --- | --- |
| TRF (%) | ADM TH8.102 (Parent) | ADM TH14.07 (TRF-R) | ADM TH1.2 (Parent) | ADM TH25.79 (TRF-R) |
| 0.1 | 0.44 | 1.18 | 1.14 | 1.44 |
| 0.2 | 0.68 | 2.98 | 1.60 | 1.62 |
| 0.4 | 1.28 | 3.74 | 1.22 | 1.90 |

Example 8

Dextrose Consumption, Growth, and L-Threonine Production in Shaker Flask Fermentation The L-threonine produced by *E. coli* strains was determined by their performance in the shaker flask fermentation. The strains being tested were grown on LB agar medium (tryptophan 10 g/L, yeast extract 5 g/L, yeast extract 5 g/L, NaCl 10 g/L, and agar 15 g/L). After 1 to 2 days of growth, cells were inoculated to 20 ml seed medium A ($K_2HPO_4$ 24.36 g/L, $KH_2PO_4$ 9.5 g/L, yeast extract 15 g/L, $(NH_4)_2SO_4$ 5 g/L, $MgSO_4$ $7H_2O$ 1 g/L, dextrose 32.5 g/L, pH 7.2) in a 250 ml baffled shaker flask. After growing at 37° C., 240 rpm shaking for 18 hours, 2 ml seed was inoculated into 20 ml of fermentation medium A (dextrose 40 g/L, citric acid 2 g/L, lactose 1 g/L, $(NH_4)_2SO_4$ 25 g/L, $KH_2PO_4$ 7.46 g/L, $MgSO_4$ $7H_2O$ 2 g L, $CaCO_3$ 20 g/L, trace metal solution 2 ml/L, pH 7.2) in a 250 ml baffled shaker flask. After cultivation at 37° C., 240 rpm shaking for 24 hours, the amount of L-threonine that had accumulated in the culture broth was analyzed by HPLC.

Under same incubation conditions indicated above, seed medium B ($MgSO_4$ $7H_2O$ 2 g/L, $(NH_4)_2SO_4$ 25 g/L, $FeSO_4$ $7H_2O$ 0.03 g/L, $MnSO_4H_2O$ 0.02 g/L $KH_2PO_4$ 2.5 g/L, citric acid 0.2 g/L, corn steep liquor 20 g/L d.s. (dissolved solid), dextrose 40 g/L, $CaCO_3$ 40 g/L, pH 7.0) and fermentation medium B ($MgSO_4$ $7H_2O$ 1.75 g/L, $(NH_4)_2SO_4$ 0.88 g/L, $K_2HPO_4$ 1.75 g/L, corn steep liquor 1.76 g/L d.s., dextrose 40 g/L, urea 20 g/L, $CaCO_3$ 17.5 g/L, pH 6.8) were also used in these studies to determine the threonine production of selected mutants.

Results of their L-threonine production and yield % in the shaker flask fermentation were shown in Table 7.

TABLE 7

| Strain | Seed/Fermentation Media | L-Threonine (g/L) | Yield % |
| --- | --- | --- | --- |
| ADM TH1.2 | A/A | 9.1 | 30.7 |
| ADM TH25.79 | A/A | 13.0 | 31.4 |

TABLE 7-continued

| Strain | Seed/Fermentation Media | L-Threonine (g/L) | Yield % |
|---|---|---|---|
| ADM TH8.102 | B/B | 11.4 | 19.7 |
| ADM TH14.97 | B/B | 11.6 | 25.1 |
| ADM TH17.166 | B/B | 13.4 | 26.6 |
| ADM TH21.07 | B/B | 15.4 | 30.7 |

Example 9

L-Threonine Production in Fermentor Fermentation

The L-threonine production of E. coli strains was also determined from their performance in fermentor fermentation. The strain being tested was grown in a shaker flask medium containing 30 g/L of tryptic soy broth and 5 g/L of yeast extract. About 1.5 ml of culture was inoculated into a 2 L baffled shake flask containing 0.5 ml shaker flask medium and incubated at 37° C. and 220 rpm for 8 hours. About 0.9 ml of the shaker flask culture was then transferred to a 5 L fermentor containing 3.0 L of the seed/main fermentor medium (corn steep liquor 10 g/L d.s. (dissolved solids), $KH_2PO_4$ 2.5 g/L, $MgSO_4$ $7H_2O$ 0.5 g/L, $(NH_4)_2SO_4$ 0.5 g/L, $FeSO_4$ $7H_2O$ 0.03 g/L, $MnSO_4H_2O$ 0.021 g/L, anhydrous citric acid 0.192 g/L, dextrose 80 g/L). The cultivation of fermentor seed was conducted under following conditions: temperature at 39° C., air flow at 3.5 LPM, agitation at 500 rpm initially, then increased to maintain the D.O. at 20%, pH at 6.9 maintained by adding $NH_4OH_4$ and back pressure at 1-2 psi. After the completion of seed stage based on the depletion of dextrose, 315 ml of seed culture was inoculated to another 5 L fermentor containing 1.6 L of same seed/main fermentor medium as described above. The fermentation was conducted for 48 hours under the following conditions: temperature at 33° C., air flow at 3.5 LPM, agitation at 800 rpm initially, then increased to maintain the D.O. at 20%, pH at 6.9 maintained by adding $NH_4OH$, and back pressure at 1-2 psi. The fermentation culture was fed with a 50% w/w dextrose solution to maintain the dextrose level at 10 g/L in the fermentor. After 48 hours, samples were withdrawn to measure the amount of L-threonine produced using HPLC (Table 8).

TABLE 8

| Strain | Relevant Phenotype | Titers L-Threonine (g/L) | Total L-Threonine (g) | Yield % |
|---|---|---|---|---|
| ADM Kat69.9 | Parent | 5.1 | 12.9 | 2.9 |
| ADM TH8.102 | Thr-R | 68.4 | 195.5 | 25.3 |
| ADM TH14.97 | Thr-R, TRF-R | 87.6 | 265.6 | 30.7 |
| ADM TH21.97 | Thr-R, TRF-R | 96.2 | 292.2 | 35.5 |
| ADM TH1.2 | Parent | 111.0 | 412.2 | 36.8 |
| ADM TH25.79 | TRF-R | 117.3 | 442.8 | 37.4 |

We claim:

1. An isolated *E. coli* strain which is resistant to threonine raffinate comprising from 0.05% to 5% ammonium sulfate, wherein said threonine raffinate is the waste stream product generated from ion exchange operations for threonine recovery from fermentation broth; which produces between about 95 and about 150 g/L of L-threonine by about 48 hours of growth in culture; and which comprises a chromosome comprising at least one *E. coli* L-threonine operon obtained from strain ATTC Deposit No. 21277 operably linked to a non-native promoter, and wherein the threonine operon encodes a feedback-resistant aspartate kinase I-homoserine dehydrogenase I (thrA), a homoserine kinase (thrB), and a threonine synthase (thrC).

2. The isolated *E. coli* strain of claim 1 which produces between about 100 and about 140 g/L of L-threonine by about 48 hours of growth in culture.

3. The isolated *E. coli* strain of claim 2 which produces between about 110 and about 130 g/L of L-threonine by about 48 hours of growth in culture.

4. The isolated *E. coli* strain of claim 3 which produces between about 110 and about 120 g/L of L-threonine by about 48 hours of growth in culture.

5. The isolated *E. coli* strain of claim 1 which contains a defective threonine dehydrogenase gene on the chromosome.

6. The isolated *E. coli* strain of claim 1 which is resistant to borrelidin or cyclopentanecarboxylic acid.

7. An isolated *E. coli* strain which has the characteristics of the strain deposited as NRRL B-30319.

8. An isolated *E. coli* strain selected from the group consisting of:

(a) the strain deposited as NRRL B-30316;

(b) the strain deposited as NRRL B-30317; and (c) the strain deposited as NRRL B-30318.

9. The isolated *E. coli* strain of claim 1, wherein said non-native promoter is the tac promoter.

10. The isolated *E. coli* strain of claim 8, wherein the isolated *E. coli* strain is the strain deposited as NRRL B-30316.

11. The isolated *E. coli* strain of claim 8, wherein the isolated *E. coli* strain is the strain deposited as NRRL B-30317.

12. The isolated *E. coli* strain of claim 8, wherein the isolated *E. coli* strain is the strain deposited as NRRL B-30318.

13. The isolated *E. coli* strain of claim 1, wherein said non-native promoter is selected from the group consisting of the tac promoter, the lac promoter, the trp promoter, the lpp promoter, the $P_L$ promoter, and the $P_R$ promoter.

* * * * *